(12) United States Patent
Wang et al.

(10) Patent No.: US 10,267,765 B2
(45) Date of Patent: Apr. 23, 2019

(54) WIDEBAND ISOLATION DIRECTED BY ION MOBILITY SEPARATION FOR ANALYZING COMPOUNDS

(71) Applicant: Agilent Technologies, Inc., Santa Clara, CA (US)

(72) Inventors: Jun Wang, San Jose, CA (US); Ruwan T. Kurulugama, Livermore, CA (US); George Stafford, San Jose, CA (US); Gregor T. Overney, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 286 days.

(21) Appl. No.: 15/099,178

(22) Filed: Apr. 14, 2016

(65) Prior Publication Data

US 2017/0299550 A1    Oct. 19, 2017

(51) Int. Cl.
*G01N 27/62* (2006.01)
*H01J 49/00* (2006.01)

(52) U.S. Cl.
CPC .......... *G01N 27/622* (2013.01); *H01J 49/004* (2013.01); *H01J 49/0031* (2013.01)

(58) Field of Classification Search
CPC .... G01N 27/622; H01J 49/0036; H01J 49/40; H01J 49/4215
See application file for complete search history.

(56) References Cited

U.S. PATENT DOCUMENTS

| | | | |
|---|---|---|---|
| 9,897,581 B1* | 2/2018 | Prakash | G01N 30/7233 |
| 2013/0161506 A1* | 6/2013 | Ugarov | G01N 27/62 250/282 |
| 2014/0353493 A1* | 12/2014 | Mordehai | H01J 49/062 250/287 |
| 2015/0041636 A1 | 2/2015 | Giles et al. | |
| 2016/0035548 A1 | 2/2016 | Brown et al. | |
| 2016/0109424 A1* | 4/2016 | Johansen | G01N 33/6848 506/12 |
| 2017/0263431 A1* | 9/2017 | Baba | H01J 49/4225 |
| 2017/0287687 A1* | 10/2017 | Chang | H01J 49/0036 |
| 2018/0095092 A1* | 4/2018 | Baba | G01N 33/6848 |

OTHER PUBLICATIONS

Hoaglund-Hyzer, Cherokee S.; Ion Trap/Ion Mobility/ Quadrupole/ Time-of-Flight Mass Spectrometry for Peptide Mixture Analysis; Analytical Chemistry; vol. 73, pp. 177-184; Jan. 15, 2001.

* cited by examiner

*Primary Examiner* — Christine A Enad

(57) ABSTRACT

In an ion mobility-mass spectrometry (IM-MS) system, an ion mass-isolated data set is acquired by operating a mass filter to apply a mass isolation window having an m/z width such that the mass isolation window moves through a sequence of window positions, each window position being defined by an IM drift time value and an m/z ratio value. The m/z width of the mass isolation window and the sequence of window positions are determined such that the mass isolation window captures ions in a region of interest of a larger all-ions data set. The isolation window may be a wideband isolation window. In comparison to the all-ions data set, the mass-isolated data set may yield reduced ion signal interference and increased selectivity for analytes of interest.

20 Claims, 11 Drawing Sheets

WIDEBAND ISOLATION DIRECTED BY ION MOBILITY SEPARATION FOR ANALYZING COMPOUNDS

TECHNICAL FIELD

The present invention relates generally to ion mobility-mass spectrometry (IM-MS), and more specifically to data-dependent acquisition of IM-MS data that utilizes wideband ion mass isolation and/or IM trace-directed mass isolation to capture desired ions of interest.

BACKGROUND

A mass spectrometry (MS) system in general includes an ion source for ionizing components of a sample under investigation, a mass analyzer for separating the ions based on their differing mass-to-charge ratios (or m/z ratios, or more simply "masses"), an ion detector for counting the separated ions, and electronics for processing output signals from the ion detector as needed to produce a user-interpretable mass spectrum. Typically, the mass spectrum is a series of peaks indicative of the relative abundances of detected ions as a function of their m/z ratios. The mass spectrum may be utilized to determine the molecular structures of components of the sample, thereby enabling the sample to be qualitatively and quantitatively characterized. One popular type of MS is the time-of-flight mass spectrometer (TOF MS). A TOF MS utilizes a high-resolution mass analyzer (TOF analyzer). Ions may be transported from the ion source into the TOF entrance region through a series of ion guides, ion optics, and various types of ion processing devices. The TOF analyzer includes an ion accelerator that injects ions in packets (or pulses) into an electric field-free flight tube. In the flight tube, ions of differing masses travel at different velocities and thus separate (spread out) according to their differing masses, enabling mass resolution based on time-of-flight.

Ion mobility spectrometry (IMS) is a gas-phase ion separation technique in which ions produced from a sample in an ion source are separated based on their differing mobilities through a drift cell of known length that is filled with an inert gas of known composition and maintained at a known gas pressure and temperature. In low-electric field drift-type IM, the ions are urged forward through the drift cell under the influence of a relatively weak, uniform DC voltage gradient. The mobility of the ions depends largely on their collision cross-sections (CCSs) and charge states (e.g., +1, +2, or +3), and to a much lesser extent their m/z ratios. Thus, ion separation by IM is largely orthogonal to ion separation by MS. From the drift cell the ions ultimately arrive at an ion detector, and the output signals from the ion detector are processed to generate peak information useful for distinguishing among the different analyte ion species detected.

An IMS system may be coupled online with a mass analyzer, which often is a TOF analyzer. In the combined IM-MS system, ions are separated by mobility prior to being transmitted into the mass analyzer where they are then mass-resolved. Due to the significant degree of orthogonality between IM-based separation and MS-based separation, performing the two separation techniques in tandem is particularly useful in the analysis of complex chemical mixtures, including biopolymers such as polynucleotides, proteins, carbohydrates and the like. For example, the added dimension provided by the IM separation may help to separate ions that are different from each other (e.g., in shape) but present overlapping mass peaks. On the other hand, the added dimension provided by the MS separation may help to separate ions that have different masses but similar CCSs. This hybrid IM-MS separation technique may be further enhanced by coupling it with liquid chromatography (LC) or gas chromatography (GC) techniques.

An IM-MS system is capable of acquiring multi-dimensional (IM-MS) data from a sample, characterized by acquisition time (i.e., chromatographic time or retention time), ion abundance (e.g., ion signal intensity), ion drift time through the IM drift cell, and m/z ratio as sorted by the MS. The IM-MS data may be quite complex and contain a very large number of data points, and hence may be difficult to evaluate by a researcher or user of the IM-MS system. This is particularly the case when the IM-MS data are acquired from a sample containing several species of high-molecular weight (MW) (bio)polymers such as proteins, peptides, and the like.

An "all-ions" IM-MS data acquisition may be performed in which all ions produced from a sample undergo separation in the IM drift cell and subsequently in the mass analyzer, without any active filtering of specific ions being undertaken prior to the acquisition. An all-ions IM-MS data acquisition may thus be characterized as a data-independent acquisition (DIA) experiment that produces a comprehensive IM-MS analysis of the sample. However, the resulting IM-MS data is of the type noted above that is complex and difficult to evaluate.

In a data-dependent acquisition (DDA) experiment, an all-ions IM-MS data acquisition may serve as the basis for finding and selecting one or more individual analyte ions of interest for further, second-stage analysis. Such selected ions may be further analyzed by operating a mass filter to sequentially isolate the selected ions from all other ions received in the mass filter, and sequentially acquiring spectral data (particularly fragment spectra) from the isolated ions. In particular, the isolated ions may be subjected to an MS/MS analysis in which, after isolation by the mass filter, the isolated ions are fragmented into fragment ions, and the fragment ions are then transmitted through a final mass analyzer to produce fragment spectra.

To aid in the selection of candidate ions for MS/MS analysis, software programs have been developed that provide graphical user interfaces (GUIs) configured to display IM-MS data in formats helpful to the user, but such GUIs generally provide less than complete solutions for aiding in the evaluation of complex IM-MS data. Other software programs, sometimes referred to as feature finders or feature extraction software, have also been developed that execute algorithms configured to find and select analyte ions of interest from a set of all-ions IM-MS data in an automated or semi-automated manner. Such computer-executed algorithms may identify candidate ions of interest based on a variety of data-dependent criteria such as minimum signal intensity, charge state, isotope pattern, and specific m/z values provided on an inclusion list or an exclusion list. However, a complex data set often includes a significant amount of ion signal interference or background chemical noise, making the process of finding and selecting analyte ions of interest difficult even when assisted by computer-executed algorithms. Thus, some ions that would be of actual interest may be overlooked due to signal interference and/or due to being present in low abundance (and thus being obscured by noise or not meeting a prescribed signal intensity threshold).

Therefore, there is a need for providing a DDA-type method that improves the process of evaluating potentially complex spectra, such as may for example be generated from a comprehensive IM-MS analysis such as an all-ions IM-MS data acquisition.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method is provided for analyzing a sample by ion mobility-mass spectrometry (IM-MS) in an IM-MS system that includes an IM analyzer, a mass filter, a mass analyzer, and an ion detector. The method includes: providing an all-ions data set acquired from an unfiltered m/z range of ions produced from the sample, the all-ions data set comprising a collection of data points spanning an IM drift time spectrum, an m/z spectrum correlated with the IM drift time spectrum, and ion abundance values correlated with the IM drift time spectrum and the m/z spectrum; determining a region of interest in the all-ions data set for further analysis; determining a wideband isolation window to be applied by the mass filter to the ions produced from the sample, by: determining a window width of the wideband isolation window, wherein the window width is an m/z sub-range of the unfiltered m/z range of ions; and determining a sequence of window positions at which the wideband isolation window is to be applied, wherein each window position is defined by a drift time value along the IM drift time spectrum and an m/z value along the m/z spectrum, wherein the window width and the sequence of window positions are determined such that the wideband isolation window when moved through the sequence of window positions transmits ions in the determined region of interest; acquiring a wideband-isolated data set by: transmitting ions produced from the sample through the IM analyzer; before or after transmitting the ions through the IM analyzer, transmitting the ions into the mass filter; while transmitting the ions into the mass filter, operating the mass filter to apply the wideband isolation window having the determined window width, and to move the wideband isolation window through the determined sequence of window positions, wherein the mass filter outputs mass-filtered ions; transmitting the mass-filtered ions, or fragment ions produced from the mass-filtered ions, to the mass analyzer and to the ion detector, wherein the ion detector outputs ion measurement signals; and producing the wideband-isolated data set from the ion measurement signals, wherein the wideband-isolated data set comprises a collection of data points in the determined region of interest.

According to another embodiment, a method is provided for analyzing a sample by ion mobility-mass spectrometry (IM-MS) in an IM-MS system that includes an IM analyzer, a mass filter, a mass analyzer, and an ion detector. The method includes: providing an all-ions data set acquired from an unfiltered m/z range of ions produced from the sample, the all-ions data set comprising a collection of data points spanning an IM drift time spectrum, an m/z spectrum correlated with the IM drift time spectrum, and ion abundance values correlated with the IM drift time spectrum and the m/z spectrum, wherein the all-ions data set comprises two or more IM traces, and the IM traces comprise respective sub-collections of data points that map onto the all-ions data set such that the IM traces diverge from each other; selecting one or more of the IM traces for further analysis; determining a mass isolation window to be applied by the mass filter to the ions produced from the sample, by: determining a window width of the mass isolation window, wherein the window width is an m/z sub-range of the unfiltered m/z range of ions; and determining a sequence of window positions at which the mass isolation window is to be applied, wherein each window position is defined by a drift time value along the IM drift time spectrum and an m/z value along the m/z spectrum, wherein the window width and the sequence of window positions are determined such that the mass isolation window when moved through the sequence of window positions transmits ions in the one or more selected the IM traces; acquiring a mass-isolated data set by: transmitting ions produced from the sample through the IM analyzer; before or after transmitting the ions through the IM analyzer, transmitting the ions into the mass filter; while transmitting the ions into the mass filter, operating the mass filter to apply the mass isolation window having the determined window width, and to move the mass isolation window through the determined sequence of window positions, wherein the mass filter outputs mass-filtered ions; transmitting the mass-filtered ions, or fragment ions produced from the mass-filtered ions, to the mass analyzer and to the ion detector, wherein the ion detector outputs ion measurement signals; and producing the mass-isolated data set from the ion measurement signals, wherein the mass-isolated data set comprises a collection of data points in the one or more selected the IM traces.

According to another embodiment, an ion mobility-mass spectrometry (IM-MS) system includes: an IM analyzer; a mass filter, disposed either upstream of or downstream from the IM analyzer; a mass analyzer disposed downstream from the IM analyzer and the mass filter; an ion detector configured to receive ions from the mass analyzer; and a controller configured to control acquisition of a wideband-isolated data set from a sample, by controlling the mass filter to apply a wideband isolation window to ions produced from the sample such that the wideband isolation window moves through a sequence of window positions effective to capture IM-MS data limited to a region of interest in an all-ions data set, wherein: the all-ions data set comprises a collection of data points previously acquired from an unfiltered m/z range of ions produced from the sample, the collection of data points spanning an IM drift time spectrum, an m/z spectrum correlated with the IM drift time spectrum, and ion abundance values correlated with the IM drift time spectrum and the m/z spectrum; the wideband isolation window has a window width corresponding to an m/z sub-range of the unfiltered m/z range of ions; and each window position is defined by a drift time value along the IM drift time spectrum and an m/z value along the m/z spectrum.

According to another embodiment, an ion mobility-mass spectrometry (IM-MS) system includes: an IM analyzer; a mass filter, disposed either upstream of or downstream from the IM analyzer; a mass analyzer disposed downstream from the IM analyzer and the mass filter; an ion detector configured to receive ions from the mass analyzer; and a controller configured to control acquisition of a mass-isolated data set from a sample, by controlling the mass filter to apply a mass isolation window to ions produced from the sample such that the mass isolation window moves through a sequence of window positions effective to capture IM-MS data limited to one or more selected IM traces of an all-ions data set, wherein: the all-ions data set comprises a collection of data points previously acquired from an unfiltered m/z range of ions produced from the sample, the collection of data points spanning an IM drift time spectrum, an m/z spectrum correlated with the IM drift time spectrum, and ion abundance values correlated with the IM drift time spectrum and the m/z spectrum, wherein the all-ions data set further comprises two or more IM traces, the IM traces comprising respective sub-collections of data points that map onto the all-ions data set such that the IM traces diverge from each other; the mass isolation window has a window width corresponding to an m/z sub-range of the unfiltered m/z range of ions; and each window position is defined by a drift time value along the IM drift time spectrum and an m/z value along the m/z spectrum.

According to another embodiment, an ion mobility-mass spectrometry (IM-MS) system includes at least a processor and a memory configured for performing all or part of any of the methods disclosed herein.

According to another embodiment, an ion mobility-mass spectrometry (IM-MS) system includes: a controller; and an ion detector communicating with the controller, wherein the IM-MS system is configured for performing all or part of any of the methods disclosed herein.

According to another embodiment, a non-transitory computer-readable storage medium includes instructions for performing all or part of any of the methods disclosed herein.

According to another embodiment, a system includes the computer-readable storage medium.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

As used herein, a "data set" or "data array" generally refers to a collection of data, or data points, organized or arranged in a predefined or logical manner. The data points may be permanently or temporarily stored in an electronic memory or a non-transitory computer-readable (or machine-readable) medium, with each data point located at a known address and accessible by appropriately configured electronics. Alternatively or additionally, as the context of the description herein may dictate, a "data set" or "data array" may refer to a visual representation of the collection of all or part of the data points, as may be implemented as a graph, plot, map, or the like, and displayed on a visual output device (e.g., computer display screen) or printed out or drawn on paper or the like.

As used herein, the abbreviations "2D," "3D," and "4D" denote "two-dimensional," "three-dimensional," and "four-dimensional," respectively.

Figure 1:
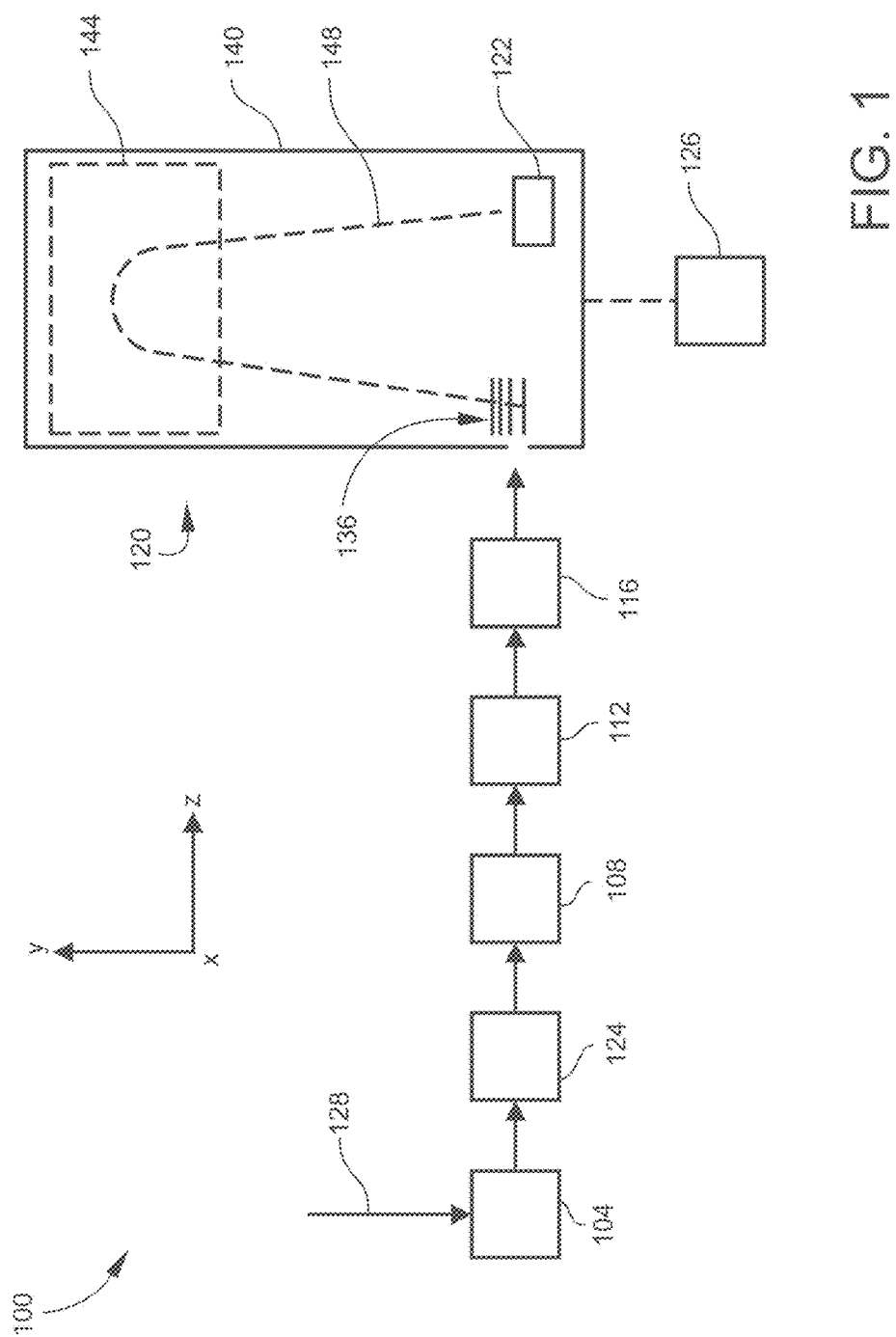
FIG. 1 is a schematic view of an example of an ion mobility spectrometry-mass spectrometry (IM-MS) system according to an embodiment disclosed herein, which may be utilized in the implementation of the subject matter described herein.

FIG. 1 is a schematic view of an example of an ion mobility-mass spectrometry (IM-MS) system 100 according to an embodiment, which may be utilized in the implementation of the subject matter described herein. The operation and design of various components of the IMS-MS are generally known to persons skilled in the art and thus need not be described in detail herein. Instead, certain components are briefly described to facilitate an understanding of the subject matter presently disclosed.

The IM-MS system 100 may generally include, in series of ion process flow, an ion source 104, an IM analyzer (or separating device) 108, a mass filter 112, an ion fragmentation device 116, a mass analyzer 120, and an ion detector 122. Alternatively, the mass filter 112 may precede the IM analyzer 108. The IM-MS system 100 may also include an ion trap 124 between the ion source 104 and the IM analyzer 108 for accumulating and periodically releasing ions in packets (pulses) on command. The configuration of the ion trap 124 may be based on, for example, an ion funnel, a 2D (linear) multipole electrode arrangement, or a 3D electrode arrangement. Alternatively, the ion source 104 may be configured to provide the functions of ion accumulation and pulsing, in which case a separate ion trap 124 may not be provided. The IM-MS system 100 may also include a vacuum system (ports, conduits, pumps, and associated components, not shown) for maintaining various interior regions of the IM-MS system 100 at controlled, sub-atmospheric pressure levels and removing non-analytical neutral molecules from the ion path through the IM-MS system 100. The IM-MS system 100 may also include a controller (or system controller, or computing device) 126 as described further herein. As appreciated by persons skilled in the art, the IM-MS system 100 may also include various ion optics along the ion path for controlling or manipulating (e.g., focusing, shaping, steering, cooling, accelerating, decelerating, slicing, etc.) the ion beam.

Generally, the ion source 104 may be any type of continuous-beam or pulsed ion source suitable for producing analyte ions for spectrometry, including atmospheric pressure ionization (API) sources and vacuum ionization sources. Examples of ion sources include, but are not limited to, electrospray ionization (ESI) sources, photo-ionization (PI) sources, electron ionization (EI) sources, chemical ionization (CI) sources, field ionization (FI) sources, field desorption (FD) sources, plasma-based or corona discharge-based sources, laser desorption ionization (LDI) sources, and matrix-assisted laser desorption ionization (MALDI) sources. Sample material to be analyzed may be introduced to the ion source 104 by any suitable means, including hyphenated techniques in which the sample material is an output 128 of an analytical separation instrument such as, for example, a gas chromatography (GC) or liquid chromatography (LC) instrument (not shown).

In a typical but not exclusive embodiment, the IM analyzer 108 is a low-field, drift-type IM analyzer that includes a drift cell enclosed in a chamber. The chamber is filled with an inert drift gas (e.g., argon, nitrogen, etc.) maintained at a controlled drift gas pressure ranging from, for example, 1 to 10 Torr. The drift cell includes a series of (typically ring-shaped) drift cell electrodes spaced along the axis that apply a typically uniform DC voltage gradient along the longitudinal axis of the drift cell. The axial DC voltage gradient moves the ions through the drift cell in the presence of the drift gas, whereby the ions become separated in time based on their different collision cross-sections (CCSs) as appreciated by persons skilled in the art. The controller 126 may calculate the "drift time" taken by each ion to traverse the length of the drift cell based on the arrival time of the ion measured at the ion detector 122. The time scale of IM separation is typically milliseconds (ms).

In a typical but not exclusive embodiment, the mass filter 112 is configured as a linear quadrupole ion guide. In such configuration, the mass filter 112 includes a set of four parallel rod-shaped electrodes positioned at a radial distance from the central axis of the mass filter 112, and circumferentially spaced from each around the central axis so as to surround an axially elongated interior mass filter volume leading from an ion entrance end to an axially opposite ion exit end. To implement mass filtering, both radio frequency (RF) potentials and direct current (DC) potentials are applied between the quadrupole electrodes so as to generate a composite RF/DC electric field effective for limiting the extent of motions of ions of selected m/z ratios in directions radial to the central axis. Under the constraints imposed by this ion confining field, ions transmitted through the entrance end travel through the mass filter volume in complex trajectories around the central axis and generally in the resultant direction of the exit end. However, the operating parameters of the RF/DC field are set so as to impose m/z-dependent stability limits on the motions of ions in the mass filter volume. The result is that only ions of selected m/z ratios are able to travel through the entire axial length of the mass filter 112 in stable trajectories focused along the central axis, and thereby pass through the exit end. On the other hand, ions of other (non-selected) m/z ratios have unstable trajectories. The amplitude of the radial oscillations of unstable ions grows as they travel through the mass filter 112 until they are no longer able to be contained by the ion confining field. Consequently, these non-selected, unstable ions are removed from the mass filter volume and do not reach the exit end of the mass filter 112.

Thus, the mass filter 112 may operate as a bandpass mass filter in which the operating parameters of the RF/DC field dictate the width ($\Delta$m/z) of the m/z passband, as well as the low m/z cutoff value and the high m/z cutoff value of the m/z passband. In the present disclosure, the m/z passband imposed by the mass filter 112 is referred to as an ion mass (m/z) isolation window. Conventionally and typically, a mass filter is operated to provide an isolation window having a very narrow width (m/z passband) spanning only a single or a few m/z values, for the purpose of achieving a high level of mass selectivity. According to embodiments of the present disclosure, however, the mass filter 112 may operate with a wideband isolation window having a width (or "window width") spanning tens, hundreds, or thousands of m/z values. For example, the mass filter 112 may be set to transmit ions in an isolation window from 100 m/z to 1100 m/z, or 150 m/z to 2000 m/z, or 200 m/z to 3000 m/z, etc. In some embodiments, the window width may be at least 5 m/z, at least 20 m/z, at least 50 m/z, at least 100 m/z, at least 250 m/z, at least 500 m/z, or greater. In some embodiments, a window width of at least 20 m/z may be considered to be a wideband window width.

The mass filter 112 may also operate in an RF-only mode. In this mode, the mass filter 112 operates solely as a linear ion guide, transmitting all ions through its volume without actively filtering the ions. In the present context, the phrase "transmitting all ions" encompasses "transmitting substantially all ions" or "transmitting essentially all ions," when taking into account the possibility that in practice some ions (e.g., at an extreme end of the range of m/z values produced from a sample) may not successfully reach the exit end of the mass filter 112 even in the absence of actively applied mass filtering.

In a typical but not exclusive embodiment, the ion fragmentation device 116 is configured as a collision cell that fragments ions by collision-induced dissociation (CID). In such configuration, the ion fragmentation device 116 may include a linear multipole (e.g., hexapole, octopole, etc.) ion guide enclosed in a chamber filled with an inert collision gas (e.g., argon, nitrogen, etc.) to a pressure effective for CID. RF potentials applied to the multipole ion guide electrodes focus the ions toward the central axis of the ion fragmentation device 116, while an axial DC voltage applied across the length of the ion fragmentation device 116 pushes the ions forward through the ion fragmentation device 116. Precursor ions (or "parent" ions) colliding with the collision gas molecules with sufficient energy will fragment into fragment ions (or "product" or "daughter" ions). Like the mass filter 112, the ion fragmentation device 116 may also operate in an RF-only mode, transmitting ions through its volume under conditions that do not cause fragmentation. In other embodiments, the ion fragmentation device 116 may have a configuration other than a CID-based device. For example, the ion fragmentation device 116 may be configured to perform electron capture dissociation (ECD), electron transfer dissociation (ETD), infrared multiphoton dissociation (IRMPD), etc.

Generally, the mass analyzer 120 is a device configured for separating analyte ions on the basis of their respective m/z ratios. In a typical but not exclusive embodiment, the mass analyzer 120 is a time-of-flight (TOF) analyzer, which includes an ion accelerator 136 leading into an electric field-free TOF flight region enclosed by an evacuated (e.g., $10^{-4}$ to $10^{-9}$ Torr) TOF flight tube 140. In the illustrated embodiment, the ion accelerator 136 is an orthogonal ion accelerator that receives ions along a drift (z) axis and accelerates ions into the flight tube 140 along an acceleration (y) axis. Also in the illustrated embodiment, the TOF analyzer has a reflectron configuration in which an electrostatic ion mirror 144 (also known as a reflectron or Mamyrin mirror) is positioned at an opposite axial end (relative to the y-axis) of the flight tube 140 relative to the ion accelerator 136 and the ion detector 122. This configuration results in a lengthened ion flight path 148 along which ions pass through the axial length of the flight tube 140 twice due to being turned around by the ion mirror 144. In operation, the ion accelerator 136 accelerates (injects) discrete packets of ions into the flight tube 140 at a predetermined pulsing rate (or firing rate). The TOF injection pulses typically occur on a much faster time scale (microseconds (µs)) than the IM injection pulses (milliseconds (ms)). As the TOF injection rate (frequency) is thus typically much higher than the IM injection rate (frequency), many TOF injection pulses occur during the period between two sequential IM injection pulses. Each ion packet injected into the flight tube 140 may include a range of ion masses, depending on how the preceding mass filter 112 and ion fragmentation device 116 are being operated. In each ion packet, ions of different masses (m/z ratios) travel through the flight tube 140 at different velocities and thus have different overall times-of-flight, i.e., ions of smaller masses travel faster than ions of larger masses. Thus, each ion packet spreads out (is dispersed) in space in accordance with the time-of-flight distribution. The ion detector 122 detects and records the time that each ion arrives at (impacts) the ion detector 122. A data acquisition process implemented by the controller 126 correlates the recorded times-of-flight with m/z ratios.

For illustrative purposes, the present description is based on the example of the mass analyzer 120 being a TOF analyzer. Depending on the embodiment or application, however, other types of mass analyzers may be suitable. Examples include, but are not limited to, multipole electrode structures (e.g., quadrupole mass filters, linear ion traps, three-dimensional Paul traps, etc.), electrostatic traps (e.g. Kingdon, Knight and ORBITRAP® traps), and ion cyclotron resonance (ICR) or Penning traps (such as utilized in Fourier transform ion cyclotron resonance mass spectrometry (FT-ICR or FTMS)), electric field sector instruments, magnetic field sector instruments, etc.

The ion detector 122 may, for example, be an electron multiplier (EM), micro-channel plate (MCP) detector, etc.

The schematically depicted controller (or computing device) 126 may represent one or more modules, control units, components, or the like configured for controlling, monitoring and/or timing the operation of various devices that may be provided in the IM-MS system 100 such as, for example, the ion source 104, ion trap 124 (if provided), IM analyzer 108, mass filter 112, ion fragmentation device 116, mass analyzer 120, ion detector 122, vacuum system, ion optics, sample introduction device, upstream LC or GC instrument, etc. One or more modules of the controller 126 may be, or be embodied in, for example, a computer workstation, desktop computer, laptop computer, portable computer, tablet computer, handheld computer, mobile computing device, personal digital assistant (PDA), smartphone, etc. The controller 126 may also schematically represent all electronic components not specifically shown in FIG. 1 that may be needed for practical operation of the IM-MS system 100, such as, for example, voltage sources, timing controllers, clocks, frequency/waveform generators, processors, logic circuits, memories, databases, etc. The controller 126 may also be configured for receiving the ion measurement signals from the ion detector 122 and performing tasks relating to data acquisition and signal analysis as necessary to generate chromatograms, drift spectra, and mass spectra characterizing the sample under analysis. The controller 126 may also be configured for providing and controlling a user interface that provides screen displays of spectrometric data and other data with which a user may interact, as described below. The controller 126 may also be configured for executing data processing algorithms such as feature finders. The controller 126 may include one or more reading devices on or in which a non-transitory or tangible computer-readable (machine-readable) medium may be loaded that includes instructions for performing all or part of any of the methods disclosed herein. For all such purposes, the controller 126 may be in electrical communication with various components of the IM-MS system 100 via wired or wireless communication links (as partially represented by a dashed line between the controller 126 and the mass analyzer 120). Also for these purposes, the controller 126 may include one or more types of hardware, firmware and/or software, as appreciated by persons skilled in the art.

A general example of operating of the IM-MS system 100 to acquire spectral data from a sample will now be described. First, the sample is introduced into the ion source 104 and the ion source 104 ionizes the sample, thereby producing analyte ions from the compounds of the sample spanning a full range of m/z values. The ion source 104 accumulates the ions for a period of time and then ion optics inject discrete ion packets sequentially into the IM analyzer 108. Alternatively, the ion trap 124 may be provided to implement the functions of ion accumulation and injection. Each ion packet at this stage spans the full range of m/z values produced in the ion source 104. The ion packets drift through the IM analyzer 108 in the presence of the drift gas under the influence of the electric field gradient established by the drift cell electrodes, and become spread out in time and space in accordance with the mobility distribution of the ions, as described elsewhere herein.

The IM-separated ions exit the IM analyzer 108 and are transmitted into the mass filter 112. During any given period of time, the mass filter 112 may be set to operate in either an all-ions mode or an ion mass isolation mode, which may be a "wideband" isolation mode as described herein. In the all-ions mode, the mass filter 112 allows all ions (ions of all m/z values) to pass through the mass filter 112 to the ion fragmentation device 116 without actively mass-filtering the ions. In the wideband isolation mode, the mass filter 112 applies the wideband isolation window described herein to allow only a sub-range (of the full, i.e., initially unfiltered, m/z range of ions that entered the mass filter 112) of the ions to pass through the mass filter 112 to the ion fragmentation device 116. The mass filter 112 may also operate in a conventional narrowband isolation mode in which it passes only one or a few target ions to the ion fragmentation device 116, and which is distinguished from the wideband isolation mode described herein.

For any given ion packet, the ion fragmentation device 116 may be set to operate in either a non-fragmentation mode or a fragmentation mode. In the non-fragmentation mode, the fragmentation device 116 transmits the ions received from the mass filter 112 to the mass analyzer 120 without fragmenting the ions. In the fragmentation mode, the fragmentation device 116 actively causes fragmentation of the (precursor) ions, and then transmits the resulting fragment ions (and possibly non-fragmented precursor ions) to the mass analyzer 120.

The mass analyzer 120 separates the ions according to m/z value before the ions arrive at the ion detector 122. The ion detector 122 counts the ions as they arrive and measures their times of arrival, and outputs ion measurement signals to the controller 126 indicative of these ion detection events. Data acquisition/signal conditioning components of the controller 126 digitize and record the ion measurement signals. Based on this raw ion measurement data, the controller 126 calculates IM drift time, m/z ratio, and corresponding ion abundance for each ion detected, and produces a multi-dimensional (IM-MS) data set or array comprising a collection of data points corresponding to all ions detected during the IM-TOF acquisitions performed. Each data point is defined by a drift time value, an m/z value corresponding to this drift time value, and an ion abundance value corresponding to these drift time and m/z values. The data points collectively span a drift time vs. abundance spectrum and also a corresponding m/z vs. abundance spectrum. These spectra may be arranged collectively as drift time vs. m/z vs. abundance spectra in a 3D data set (or array) or a color-coded 2D plot (such as a heat map). If the IM-MS system 100 is operated in the all-ions mode, the resulting IM-MS data set captures (covers) the full m/z range of ions that were injected into the IM analyzer 108, or the full range of fragment ions produced from the precursor ions in the case where the fragmentation device 116 is operated in the fragmentation mode. If on the other hand the IM-MS system 100 is operated in a mass isolation mode such as the wideband isolation mode (i.e., with the isolation window applied by the mass filter 112), the resulting IM-MS data set captures a sub-range of the full m/z range of ions that were injected into the IM analyzer 108 (or fragment ions produced from the sub-range of precursor ions in the case where fragmentation is implemented). In either case, the controller 126 may store the IM-MS data set in memory. The controller 126 may also display the IM-MS data set as visual graphs, plots, or maps via a graphical user interface (GUI), such as a "browser" that may enable the user to interact with the displayed data in various ways.

Figure 2:
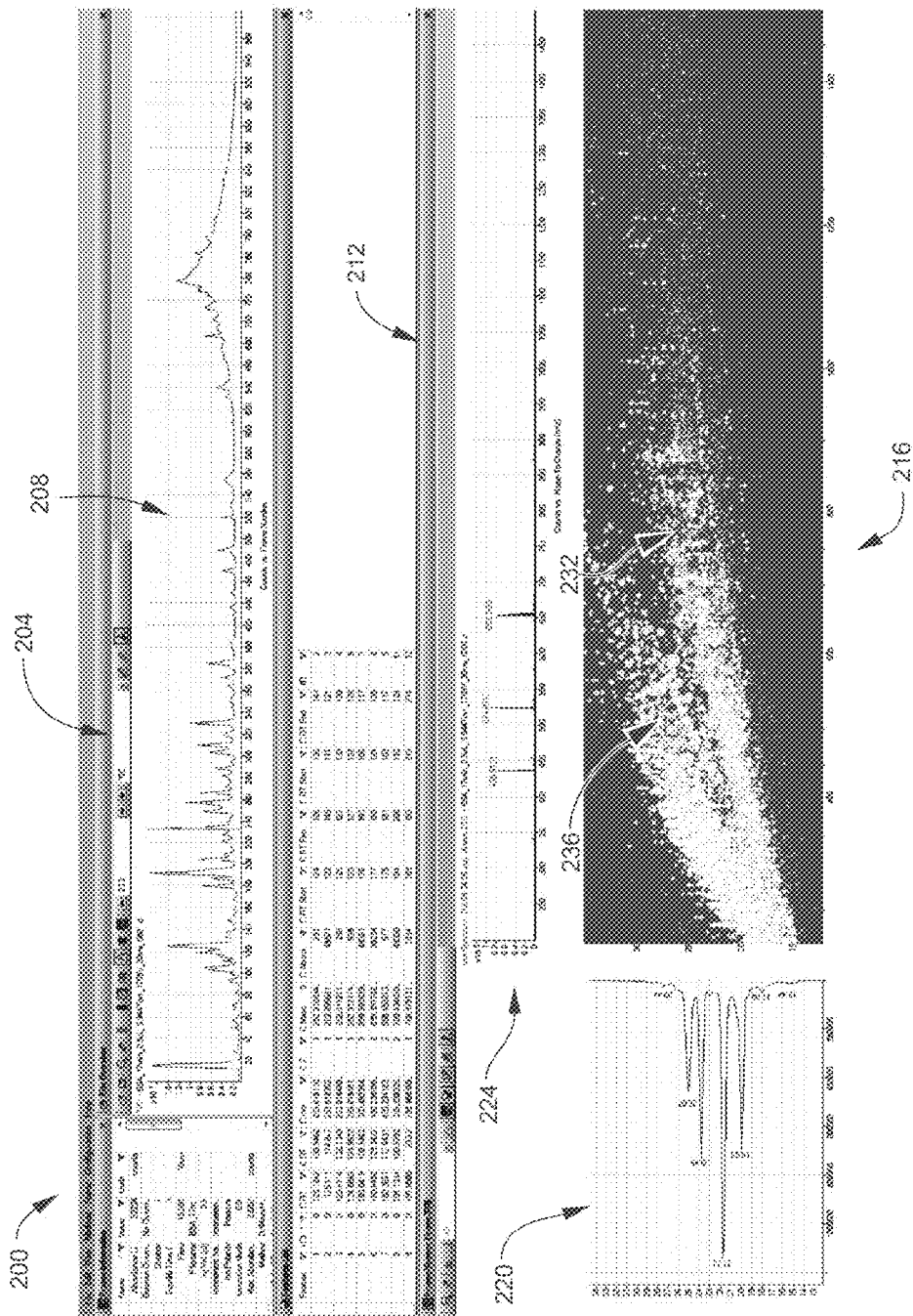
FIG. 2 is an example of a screen display provided as part of a user interface, displaying an all-ions IM-MS data set acquired by an IM-MS system according to an embodiment disclosed herein.

FIG. 2 illustrates an example of a screen display 200 that may be provided as part of a GUI. The screen display 200 includes (displays) an example of a graphical representation of an IM-MS data set acquired by an IM-MS system (e.g., the IM-MS system 100 described above and illustrated in FIG. 1) during analysis of a complex sample. In the illustrated example, the data set is an all-ions data set acquired from an IM-MS analysis of a sample of bovine serum albumin (BSA) digest transferred into the IM-MS system from an LC column. The screen display 200 may be presented to a user, for example, on a user output device (e.g., a display screen) controlled by a computing device (e.g., the controller 126 described above and illustrated in FIG. 1).

The screen display 200 may display one or more display areas containing different types of information pertaining to the IM-MS system and/or the sample analysis performed thereby. The screen display 200 may be, or be part of, a GUI provided by application software specifically configured for implementing the subject matter disclosed herein, which may be controlled by an operating system such as, for example, the Microsoft Windows® operating system. Thus, a display area may be, or be part of, a "window" that may be manipulated in a variety of ways, often with the use of a pointing device such as a mouse as appreciated by persons skilled in the art. In the illustrated example, one display area 204 includes a chromatogram 208 and another display area 212 includes three display regions: a pseudo-3D graph or heat map 216 plotting drift time vs. m/z vs. abundance, a drift time spectrum 220, and an m/z spectrum 224. These two display areas 204 and 212 cooperatively provide 4D data (abundance versus acquisition time versus drift time versus m/z ratio) acquired from the sample analysis performed by the IM-MS system. The display areas may be configured for aiding visualization of the 4D data by showing a set of 2D, 3D, and/or pseudo-3D "slices" or "projections" of the 4D data, which a user can more easily comprehend.

The chromatogram 204 in this example is an unfiltered total ion current (TIC) chromatogram, but alternatively may be a base peak chromatogram or an extracted ion current (EIC) chromatogram, as appreciated by persons skilled in the art. The chromatogram 204 is a plot of ion measurement signal intensity (in counts, as detected by the ion detector) as a function of acquisition time (i.e., chromatographic time or retention time). Acquisition time relates to the overall time duration of a sample analysis over which ion measurement data was acquired. In the illustrated example, acquisition time is scaled in "frame numbers" but alternatively may be scaled in minutes or seconds. As used herein, a "frame" is a set of m/z spectra acquired at the same nominal acquisition time, with each m/z spectrum corresponding to a different drift time. One frame is equivalent to one point in acquisition time (e.g., retention time along a chromatogram).

The heat map 216 displays a slice of IM-MS data extracted from a selected frame of the chromatogram 204, in this example frame #233. In the heat map 216, m/z ratio is plotted along one axis (the x-axis, or horizontal axis, in the illustrated example), IM drift time is plotted along an orthogonal axis (the y-axis, or vertical axis, in the illustrated example), and ion abundance is shown as a color at any given x-y coordinate in the graph containing ion measurement data. Generally, different (varying) abundance values may be displayed as different (varying) colors according to any desired color-coding scheme. The drift time spectrum 220 plots ion signal intensity as a function of drift time, and is displayed as a 2D projection (or "side plot") from the drift time axis of the heat map 216. The ion abundance (signal intensity) shown in the drift time spectrum at any given drift time point is summed over the m/z range currently visible in the heat map 216. The m/z spectrum 224 plots ion signal intensity as a function of m/z ratio, and is displayed as a 2D projection from the m/z ratio axis of the heat map 216. The ion abundance shown in the mass spectrum at any given m/z ratio value is summed over the drift range currently visible in the heat map 216.

As described earlier in this disclosure, in a data-dependent acquisition (DDA) experiment, an all-ions IM-MS data set may serve as the basis for finding and selecting one or more individual analyte ions of interest for further analysis. Such selected ions may be further analyzed by operating the mass filter to isolate the selected ions from all other ions received in the mass filter, and acquire spectral data (particularly fragment spectra) from these isolated ions. Computer-executed algorithms may be utilized to assist in finding and selecting analyte ions of interest. However, as evident from the heat map 216 shown in FIG. 2, an all-ions IM-MS data set may be quite complex and contain a very large number of data points, particularly when acquired from a complex sample. The complex data set may thus include a significant amount of background chemical noise or ion signal interference, making the process of finding and selecting analyte ions of interest difficult even when assisted by computer-executed algorithms.

According to an aspect of the present disclosure, an IM-MS data set may be acquired by utilizing a moving wideband isolation window in a process referred to herein as wideband-isolated IM-MS data acquisition. As described above, this is accomplished by controlling the mass filter of the IM-MS system to operate in a wideband isolation mode, in which the mass filter transmits only ions having masses in a predefined sub-range (of the full m/z range of ions that entered the mass filter) corresponding to the wideband isolation window. Consequently, only those ions in the wideband isolation window are transmitted to the final mass analyzer for measurement and generation of spectra. The wideband isolation window is "moved" through IM-MS (drift time-m/z) space by varying (adjusting) the operating parameters of the mass filter, as described herein. The wideband isolation window may be moved so as to capture (cover) ions occupying a particular region or regions of interest in IM-MS space. In this way, the resulting wideband-isolated IM-MS data set is simpler than an all-ions IM-MS data set acquired from the same sample, as the spectra are focused only on the region(s) of interest.

A region of interest to which to apply the wideband isolation window may be determined (or selected) from, or based on, an all-ions IM-MS data set acquired from the sample. The determination of the region of interest may be made by implementing one or more automated and/or manual processes. The process of determination may be fully automated or partially automated (assisted) by processing the all-ions data set with the use of computer-executed algorithms, e.g., as may be embodied in an appropriately constructed software program (e.g., a feature finder). Alternatively or additionally, the process of determination may be manual. For example, a researcher may determine a region of interest by studying the all-ions data set. The researcher's evaluation of the data may be assisted through the use of a graphical interface such as described above and illustrated in FIG. 2, which displays the data in useful formats such as the above-described data plots (chromatogram 204, heat map 216, drift time spectrum 220, and m/z spectrum 224). The graphical interface may provide various tools, functionalities, and levels of user interaction that further aid the researcher in the evaluation. Examples include, but are not limited to, zooming in and out of the data plots, extracting slices or sections of the data plots, applying filters to the data plots, calculating collision cross-sections from selected data, etc.

A region of interest may include ions that are related by one or more attributes such as, for example, ions having the same charge state, ions that are isomers (e.g., ions having the same chemical formula but different chemical structures, such as structural isomers, conformers, etc.), etc. A region of interest, or a combination of regions of interest, may capture all or part of an IM trace observed in the all-ions data set. In the present context, an IM trace is a set of data points that map into a region or trend line on the IM-MS space, and is distinct from other IM traces in an observable manner. For example, two IM traces may be observed to follow different trend lines (or directions) and/or diverge away from each other. IM traces may be formed by data sets generated by, for example, charge state, conformational, and isomer trends. In the example of FIG. 2, the heat map 216 is observed to include two discernable IM traces 232 and 236.

Thus, according to an embodiment of the present disclosure, a wideband-isolated IM-MS data acquisition may be IM trace-directed. Moreover, the wideband-isolated IM-MS data acquisition may be global IM trace-directed or local IM trace-directed. In a global IM trace-directed acquisition, the regions of interest are determined so as to capture all IM traces or at least two or more selected IM traces. The regions of interest may be determined so as to capture the entire m/z range or a sub-range of the entire m/z range of the IM traces being captured, and/or the entire drift time range or a sub-range of the entire drift time range of the IM traces being captured. In a local trace-directed acquisition, the regions of interest are determined so as to capture a single selected IM trace. The regions of interest may be determined so as to capture the entire m/z range or a sub-range of the selected IM trace, and/or the entire drift time range or a sub-range of the entire drift time range of the selected IM trace.

After the region or regions of interest have been determined, the wideband isolation window that will be utilized to acquire the wideband-isolated data set is determined (or defined). The isolation window is determined/defined in terms of two parameters: (1) the width (size of the m/z passband) of the isolation window, or "window width"; and (2) the operation mode, or isolation window movement mode, by which the isolation window is to be moved through the all-ions data set during acquisition of the wideband-isolated data set. The two parameters are determined such that the movement of the isolation window will successfully cover all of the regions of interest selected from the all-ions data set, and depends on whether the wideband isolation is to be global IM trace-directed or local IM trace-directed.

The window width is described above in conjunction with the mass filter 112 illustrated in FIG. 1. For each iteration of movement of the isolation window, the isolation window width may remain constant or may vary relative to the other iterations of movement, as needed to obtain coverage of the desired region(s) of interest. For example, the overall perimeter enclosing the region or regions of interest may be an irregular shape, examples of which are the IM traces 232 and 236 shown in FIG. 2. In such case, the isolation window width may need to vary as it follows the region of interest (e.g., IM trace 232 or 236) in order to capture all of the peaks constituting that region of interest. At any position of the isolation window, the isolation window width is defined by the low and high mass cut-off points set by the mass filter. As appreciated by persons skilled in the art, the low and high mass cut-off points are controlled by the operating parameters of the mass filter. The pertinent operating parameters are typically the amplitude of the RF voltage and the magnitude of the DC voltage applied between the rod electrodes of the mass filter.

The operation mode dictates how the isolation window moves during acquisition of the wideband-isolated data set. The operation mode is based on a sequence of isolation window positions, which correspond to iterations of movement of the isolation window. Each isolation window position is defined by the drift time position and the m/z position of the centroid of the isolation window. The drift time position is a value along the drift time axis of the all-ions data set. The m/z position is a value along the m/z axis of the all-ions data set. For each isolation window position in the sequence, the drift time position depends on the timing at which the mass filter implements the isolation window, which timing is coordinated/synchronized with the operations of the other devices of the IM-MS system during acquisition of the wideband-isolated data set. Also for each isolation window position in the sequence, the m/z position of the centroid is dictated by the low and high mass cut-off points imposed by the mass filter.

Figure 3:
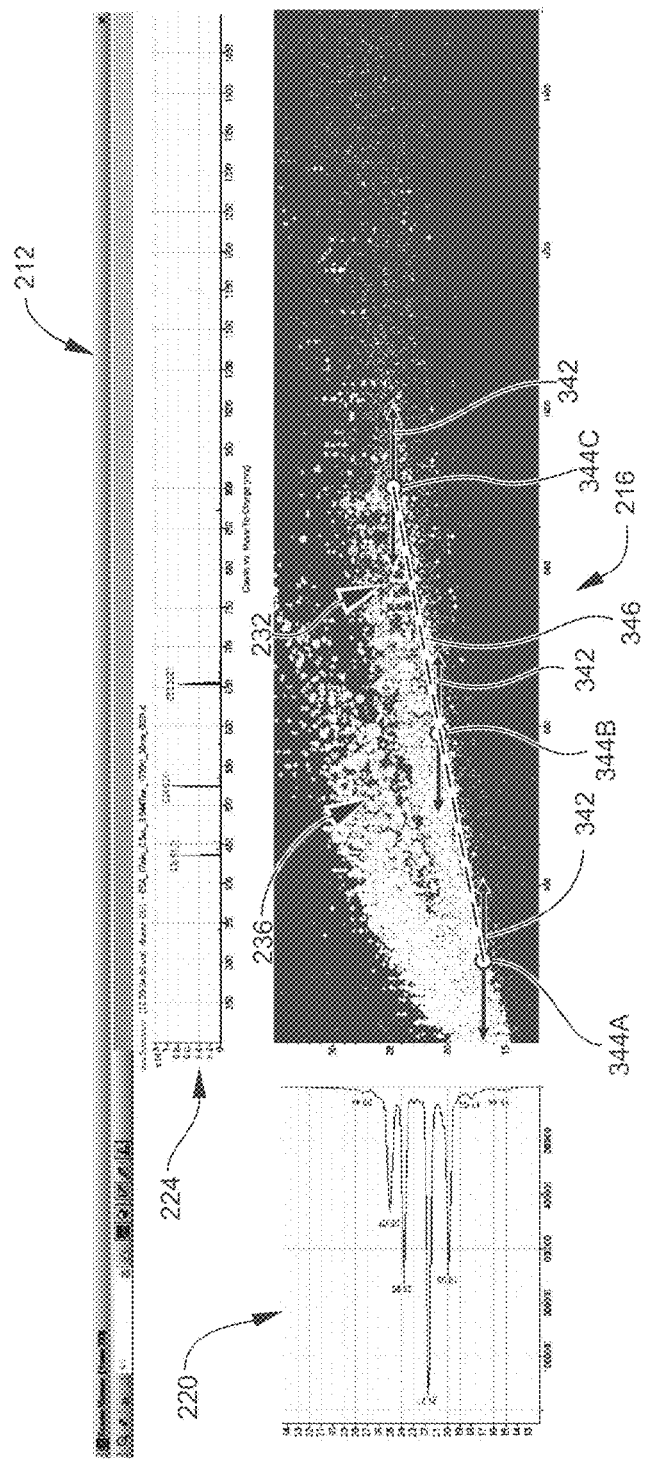
FIG. 3 is an example of a screen display that illustrates an example of an isolation window and how it may be moved through IM-MS space, according to an embodiment disclosed herein.

FIG. 3 illustrates the display area 212 of FIG. 2, and illustrates an example of an isolation window 342 and how it may be moved through the IM-MS space, in this example through the data set displayed in the heat map 216. In this example, the region of interest has been determined to be the lower IM trace 232. Thus, the isolation window width and sequence of isolation window positions are determined (and the mass filter is programmed accordingly) such that the isolation window 342 follows the lower IM trace 232, i.e., moves through the lower IM trace 232 in a way that captures all or a desired portion of the data points of the lower IM trace 232. In this example, the width of the isolation window 342 has been set to $\Delta m/z=200$. By example, three positions of the isolation window 342 are illustrated. At these positions, the centroid of the isolation window 342 is labeled 344A, 344B, and 344C, respectively. Specifically, the centroid 344A is located at about 300 m/z, the centroid 344B is located at about 585 m/z, and the centroid 344C is located at about 1000 m/z. In the operation mode actually implemented in practice, the number of isolation window positions in the sequence may be less than or more than three, and often many more than three. In this example, the isolation window width is the same (remains constant) at each of the illustrated isolation window positions, but alternatively may vary from one position to another as noted above.

To capture the lower IM trace 232, the sequence may be arranged such that the isolation window 342 moves in a series of positions starting in the lower left area of the lower IM trace 232 and ending in the upper right area of the lower IM trace 232 (from the perspective of the as-displayed heat map 216). Thus in this example, the centroid 344A, 344B, 344C follows a slightly curved path through the lower IM trace 232 as indicated by a dashed line 346. More generally, the centroid of an isolation window may follow a curved path, a straight path, or a path comprising both curved and straight sections, as needed to capture all of the desired data points. Moreover the rate of change (slope) of a linear path, or the radius of curvature of a curved path, may be constant or may vary, as needed to capture all of the desired data points.

Figure 4:
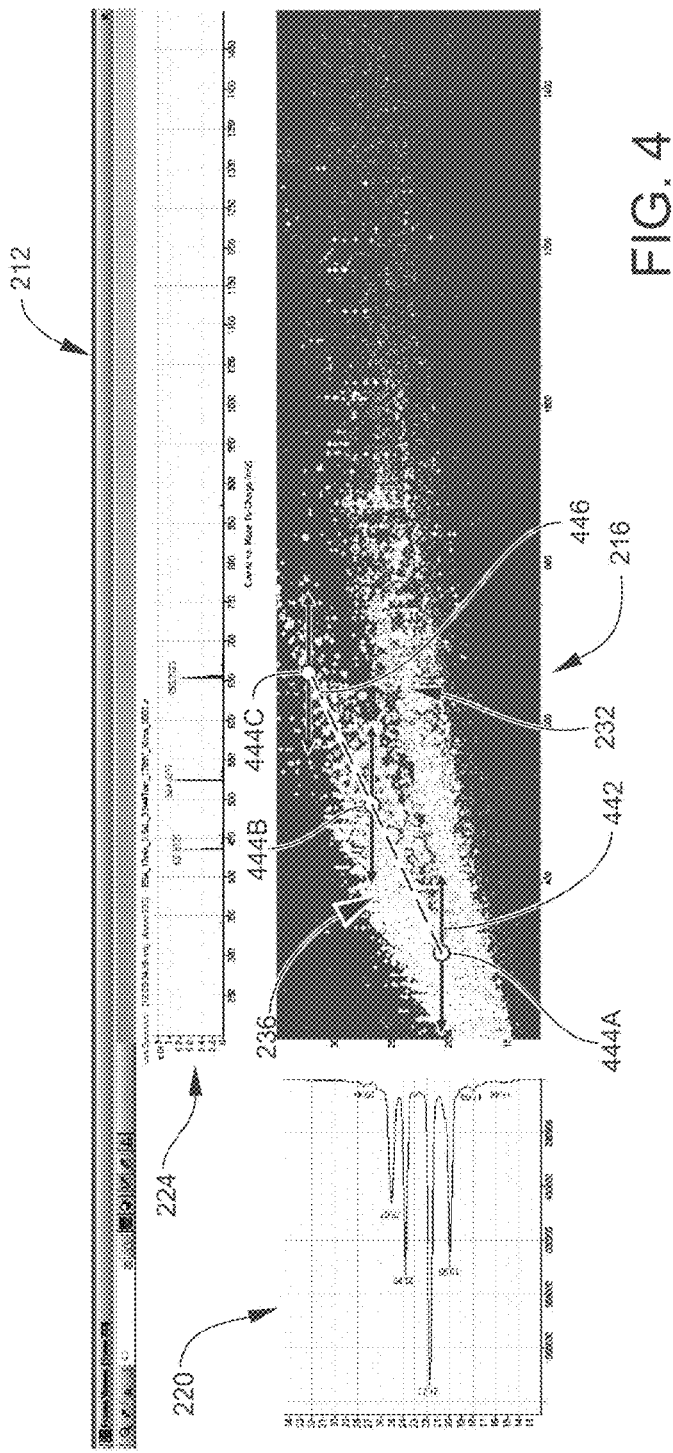
FIG. 4 is an example of a screen display that illustrates another example of an isolation window and how it may be moved through IM-MS space, according to an embodiment disclosed herein.

FIG. 4 also illustrates the display area 212 of FIG. 2, and an example of another isolation window 442 and how it may be moved through the IM-MS space. In this example, the region of interest has been determined to be the upper IM trace 236. Three positions of the isolation window 442 are illustrated, at which the centroid is labeled 444A, 444B, and 444C, respectively. To capture the upper IM trace 236, the sequence may be arranged such that the isolation window 442 follows the upper IM trace 236, e.g., moves in a series of positions starting in the lower left area of the upper IM trace 236 and ending in the upper right area of the upper IM trace 236. Thus in this example, the centroid 444A, 444B, 444C follows a curved path through the lower IM trace 232 as indicated by a dashed line 446.

FIGS. 3 and 4 illustrate examples of a local IM trace-directed wideband-isolation data acquisition. In a global IM trace-directed wideband-isolation data acquisition, the parameters (window width and operation mode) of the isolation window may be defined so as to capture all or a desired portion of both IM traces 232 and 236, or more generally two or more IM traces of a given all-ions data set. As one example of a global data acquisition, the isolation window may be programmed to move through the lower IM trace 232 (e.g., by following the path 346 shown in FIG. 3) and subsequently through the upper IM trace 236 (e.g., by following the path 446 shown in FIG. 4), or vice versa. As another example of a global data acquisition, the isolation window may be programmed to move along one or more different paths than those shown in FIGS. 3 and 4, with the width of isolation window varied as needed to capture all of the desired data points in both IM traces 232 and 236.

In some implementations of a wideband-isolation data acquisition, the operation mode of the isolation window may entail moving the isolation window in a manner such that the centroid (and thus the isolation window) is stepped across the region(s) of interest. Depending on how spread out the stepped centroids are from each other, sequentially adjacent isolation window positions may or may not overlap with each other. Moreover, gaps between sequentially adjacent isolation window positions, containing data points that are excluded from the wideband-isolation data acquisition being performed, may or may not exist. As one example of a stepped operation mode, an isolation window of width $\Delta m/z=50$ may move through the following positions: 50 m/z to 99 m/z, then 100 m/z to 149 m/z, then 150 m/z to 199 m/z, and so on. As another example of a stepped operation mode, an isolation window of width $\Delta m/z=50$ may move through the following positions: 50 m/z to 99 m/z, then 89 m/z to 138 m/z, then 128 m/z to 177 m/z, and so on. As another example of a stepped operation mode, an isolation window of width $\Delta m/z=50$ may move through the following positions: 50 m/z to 99 m/z, then 119 m/z to 168 m/z, then 188 m/z to 217 m/z, and so on. Regarding the latter two examples, it will be noted that size of the overlap or the gap need not remain constant from one position to another. Moreover, as noted above the width $\Delta m/z$ need not remain constant from one position to another.

In other implementations of a wideband-isolation data acquisition, the operation mode of the isolation window may entail moving the isolation window in a manner such that the centroid (and thus the isolation window) is scanned across the region(s) of interest. In the scanned operation mode, the isolation window is moved from one position to another in a gradual manner, i.e., in finely stepped iterations, which may entail a significant degree of overlap. As one example of a scanned operation mode, an isolation window of width $\Delta m/z=50$ may move through the following positions: 50 m/z to 99 m/z, then 55 m/z to 104 m/z, then 60 m/z to 109 m/z, as so on.

In FIGS. 3 and/or 4, the three isolation window positions shown at the centroids 344A, 344B, and 344C (or at the centroids 444A, 444B, and 444C) may correspond to a sequence defined by a stepped operation mode or a scanned operation mode.

In other implementations of a wideband-isolation data acquisition, the operation mode of the isolation window may entail programmatically moving the isolation window to follow a predefined (programmed) pattern effective to cover the regions of interest. The pattern may not necessarily follow a single path through the data set, and may not necessarily progress in a single direction only. Instead, the pattern may follow two or more discrete paths that may not be contiguous, and/or the pattern may be such that the isolation window "jumps around" to different positions. The pattern may include sections of stepping and/or scanning. Referring to FIG. 3 or 4, as one example of a patterned operation mode, one or more portions of both IM traces 232 and 236 may be captured by programming the isolation window to jump between the IM traces 232 and 236 one or more times as the isolation window progresses through the acquisition.

It will be understood that "movement" of the "position" of an isolation window does not require actual movement of the isolation window in a displayed graphical depiction of data such as shown in FIGS. 3 and 4. Instead, the term "movement" may be used as an illustrative way to describe the adjustment or variance of the operating parameters of the mass filter that results in the adjustment or variance of the m/z passband imposed by the mass filter at pre-programmed points of time. Nonetheless, as shown in FIGS. 3 and 4 the GUI may be configured to display to the user the isolation window at any position in a proposed operating mode. Moreover, the GUI may be configured to provide an animation that enables the user to visualize how the isolation window moves through a proposed region of interest according to a proposed operating mode.

Figure 5:
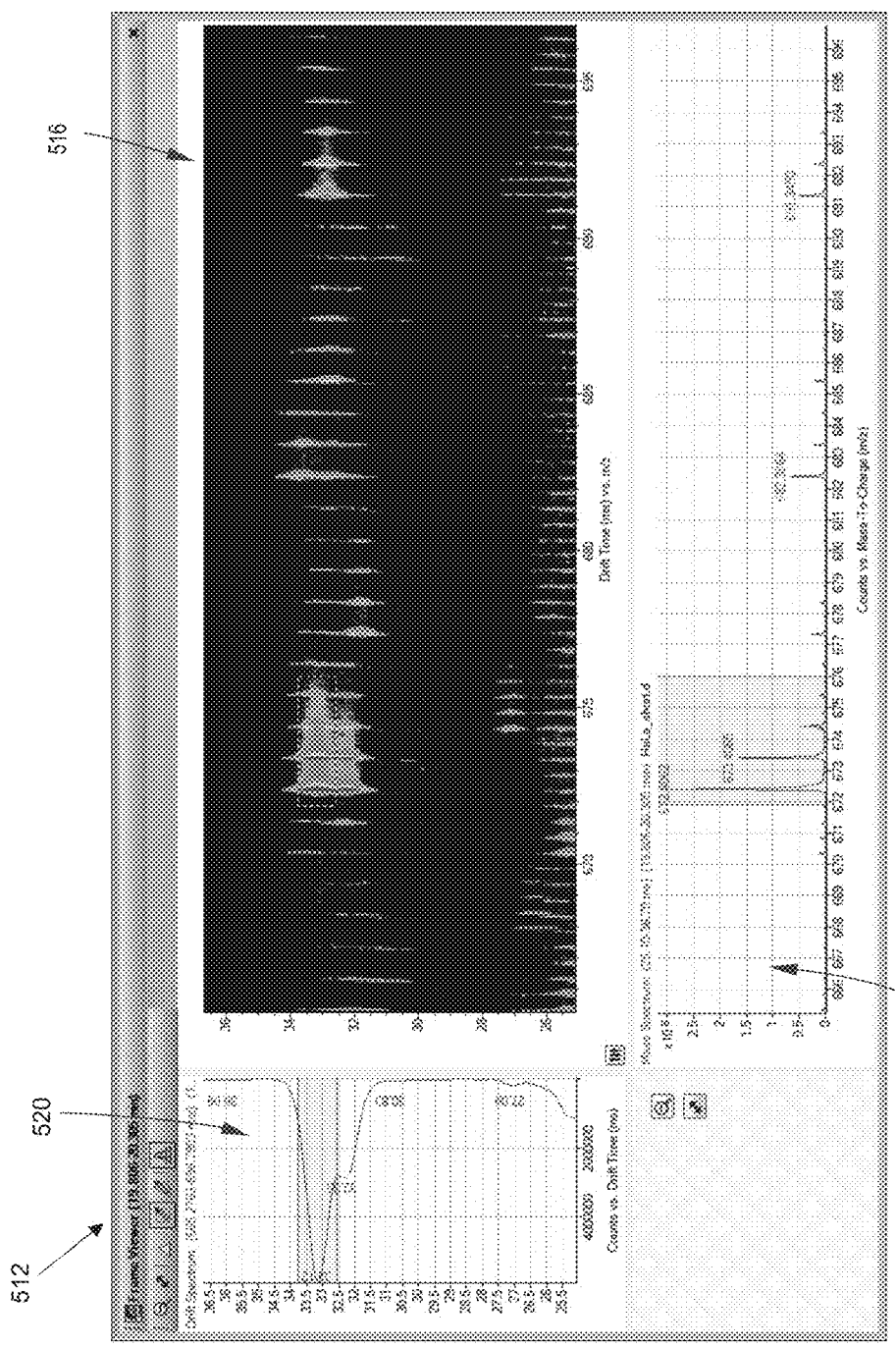
FIG. 5 is an example of a screen display that illustrates an example of a region of interest of an IM-MS data set, which may be captured by a wideband-isolated data acquisition according to an embodiment disclosed herein.

FIG. 5 is another example of a display area 512 that includes a heat map 516, drift time spectrum 520, and m/z spectrum 524. FIG. 5 illustrates an example of a determined region of interest, the boundary of which is demarcated by a dashed-line in the heat map 516. In the illustrated example, the region of interest has a rectilinear shape. More generally, the region of interest may have any polygonal shape, or rounded (e.g., circular, elliptical, etc.) shape, or irregular shape, as needed to capture all of the desired data points. Moreover, more than one region of interest may be determined or selected. Multiple regions of interest may be spaced from (may be non-contiguous with) each other, or may be contiguous with (or immediately adjacent to) each other. In one example, multiple contiguous regions of interest may be selected and then combined so as to form a larger region of interest. The dashed-line boundary displayed to the user may be the result of a computer-executed algorithm-determined region of interest, and may be a proposed region of interest that the user may accept or reject. Alternatively, the dashed-line boundary may be the result of the user selecting the region of interest by providing an input effective to define the boundary of the region of interest, such as by inputting data (e.g., entering the end points of drift time and m/z ranges via keyboard strokes) into the controller or computing device controlling the display area 512, or by operating a mouse or other pointing device to draw or trace out the boundary on the display screen in a manner common to window-type GUIs. The user may select the region of interest directly in the heat map 516, or by selecting a drift time range and m/z range from the drift time spectrum 520 and m/z spectrum 524, respectively. As indicated by shaded regions in the drift time spectrum 520 and the m/z spectrum 524, the drift time and m/z ranges defining the selected region of interest displayed in the heat map 516 may also be projected onto the drift time spectrum 520 and the m/z spectrum 524, respectively.

FIG. 5 also illustrates an example of a GUI providing a zooming function with which the user is able to focus on a selected area of a displayed data set. In this example, the data plots displayed are the result of zooming in to a narrower drift time range (25 to 36.5 ms) and m/z range (665.5 to 697.5) from a broader, more complete display of the acquired data set.

Figure 6:
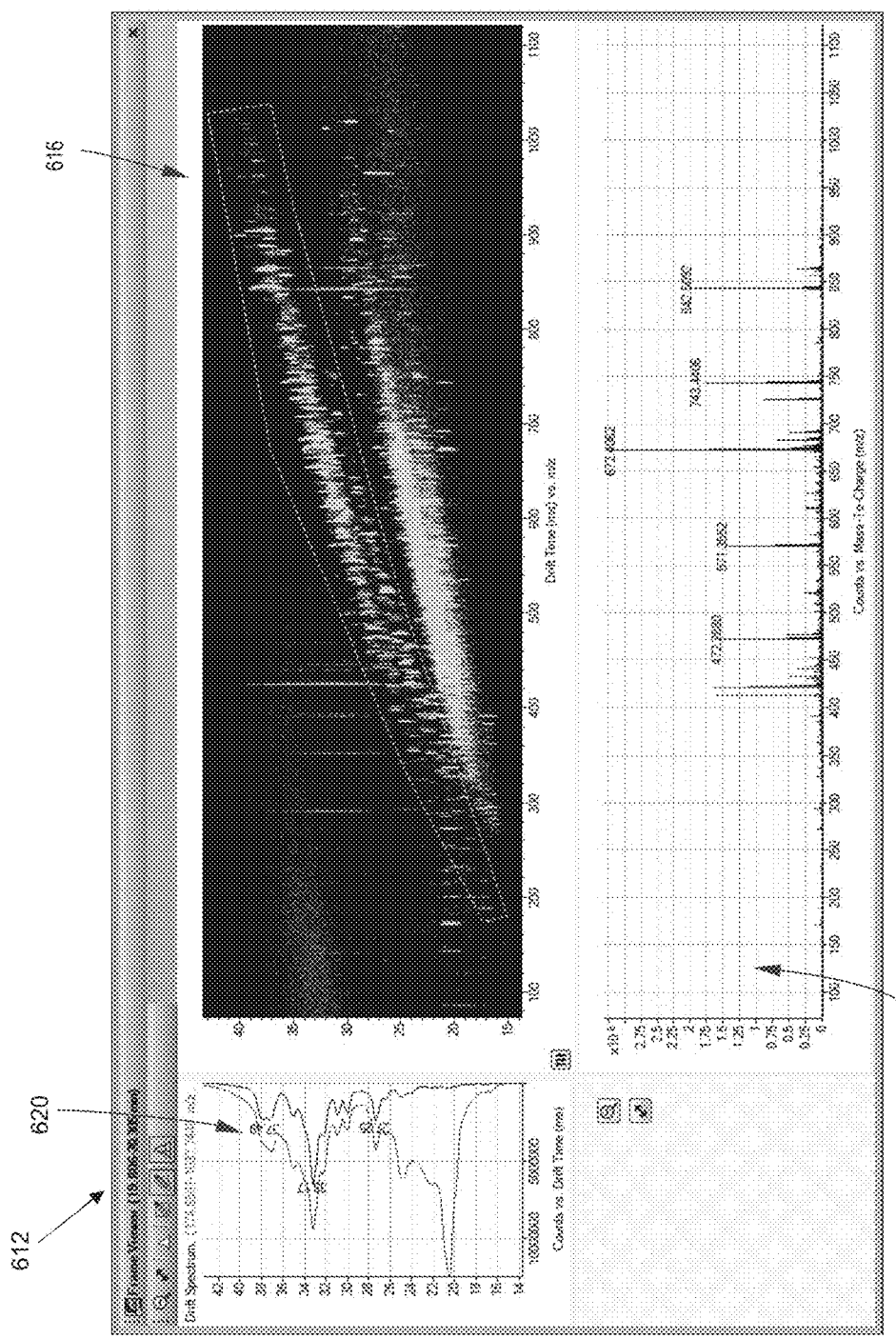
FIG. 6 is an example of a screen display that illustrates another example of a region of interest of an IM-MS data set, which may be captured by a wideband-isolated data acquisition according to an embodiment disclosed herein.

FIG. 6 is another example of a display area 612 that includes a heat map 616, drift time spectrum 620, and m/z spectrum 624. FIG. 6 illustrates an example of selecting a distinct IM trace as the region of interest. In this example the selected IM trace is enclosed by a dashed-line boundary, the shape of which is an irregular polygon in order to capture all or substantially all of the data points associated with the selected IM trace. Again, this may be the result of a computer-executed algorithm-driven determination or a user-inputted determination/selection.

After the parameters (width and operation mode) of the isolation window have been determined, the wideband-isolation data acquisition may be implemented to generate spectra from the determined region or regions of interest. Referring to FIG. 1, one or more ion packets produced from the same sample that was subjected to an all-ions IM-MS analysis (e.g., as shown in FIG. 2) are sequentially injected into and transmitted through the IM analyzer 108. The IM-separated ions exit the IM analyzer 108 and are transmitted into the mass filter 112. During the wideband-isolation data acquisition, the mass filter 112 is set to operate in the wideband isolation mode. That is, the mass filter 112 is programmed to implement the moving isolation window having the selected window width and in accordance with the selected operation mode, as the IM-separated ions elute from the drift cell. Thus, the mass filter 112 transmits only the m/z sub-ranges corresponding to the respective positions of the isolation window to the ion fragmentation device 116.

As noted above, the ion fragmentation device 116 may be set to operate in either a non-fragmentation mode or a fragmentation mode. Thus, the fragmentation device 116 either transmits the wideband-isolated ions received from the mass filter 112 to the mass analyzer 120 without actively fragmenting the ions, or produces fragment ions from the wideband-isolated ions received from the mass filter 112 and transmits the fragment ions (and possibly non-fragmented precursor ions) to the mass analyzer 120.

The mass analyzer 120 separates the ions received from the ion fragmentation device 116 according to m/z ratio, and the ion detector 122 detects the ions as they arrive from the mass analyzer 120, as described above. The controller 126 processes the ion measurement signals received from the ion detector 122 as described above, and generates a wideband-isolated IM-MS data set (or array). The wideband-isolated IM-MS data set comprises a collection of data points corresponding to all ions detected during the wideband-isolated IM-TOF acquisition. The ions detected and analyzed during the wideband-isolated IM-TOF acquisition are limited to ions populating the region or regions of interest (and/or or fragment ions produced therefrom) previously determined and delimited by the moving isolation window as described above. Thus, the spectra from the wideband-isolated IM-MS data set are characterized by reduced background ion signal interference.

In some embodiments, if desired the wideband-isolated IM-MS data set may be utilized to find and select one or more precursor ions for further investigation. Commercially available feature finder software may be utilized for this purpose. Fragment spectra from the selected parent ion(s) may then be acquired in a conventional manner, by operating the mass filter 112 with a narrow m/z range to isolate the selected parent ion(s), and operating the ion fragmentation device 116 to cause fragmentation.

Figure 7:
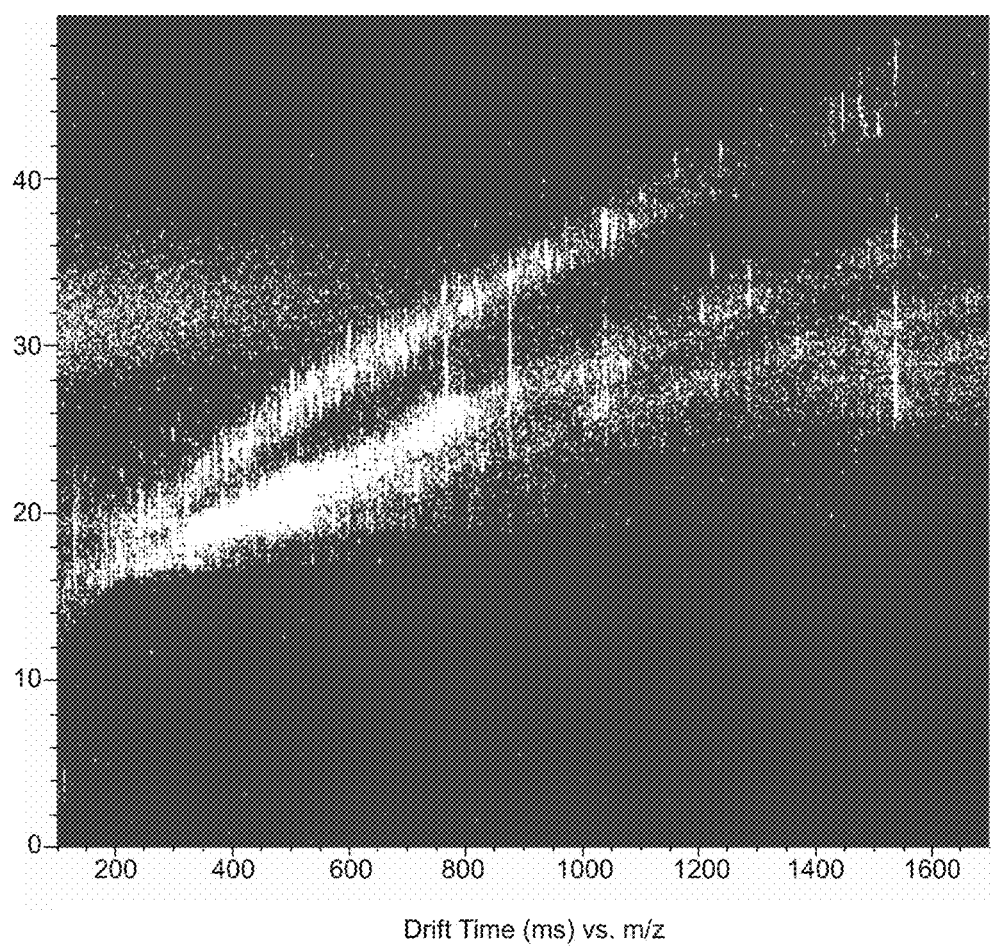
FIG. 7 is an example of a heat map representing an example of all-ions IM-MS data set acquired from a sample, in which at least three different IM traces are discernable.
Figure 8:
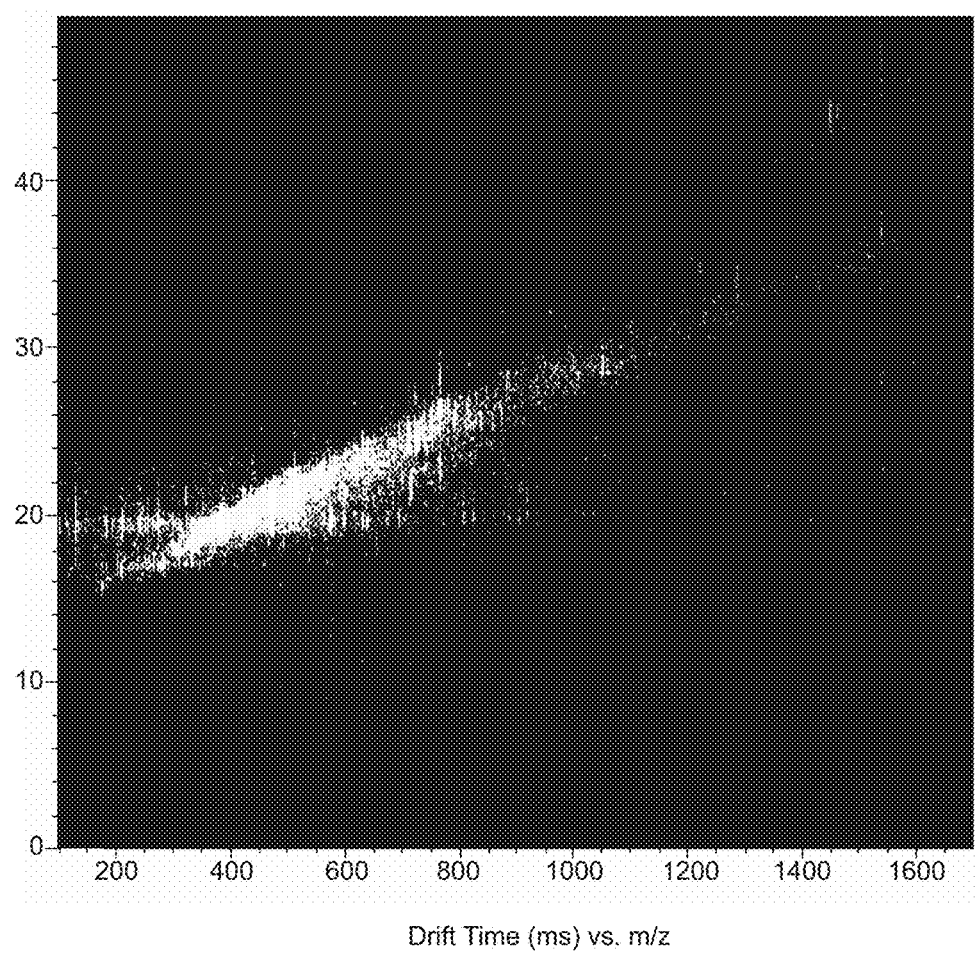
FIG. 8 is an example of a heat map representing an example of a local IM trace-directed wideband-isolated IM-MS data set acquired from the same sample associated with FIG. 8, according to an embodiment disclosed herein.

FIG. 7 is an example of a heat map representing an all-ions IM-MS data set acquired from a BSA sample. At least three different IM traces are discernable. By comparison, FIG. 8 is an example of a heat map representing a local IM trace-directed wideband-isolated IM-MS data set acquired from the same sample. In this example, the isolation window has been determined so as to capture only one of the IM traces observed in the all-ions IM-MS data set shown in FIG. 7.

Figure 9:
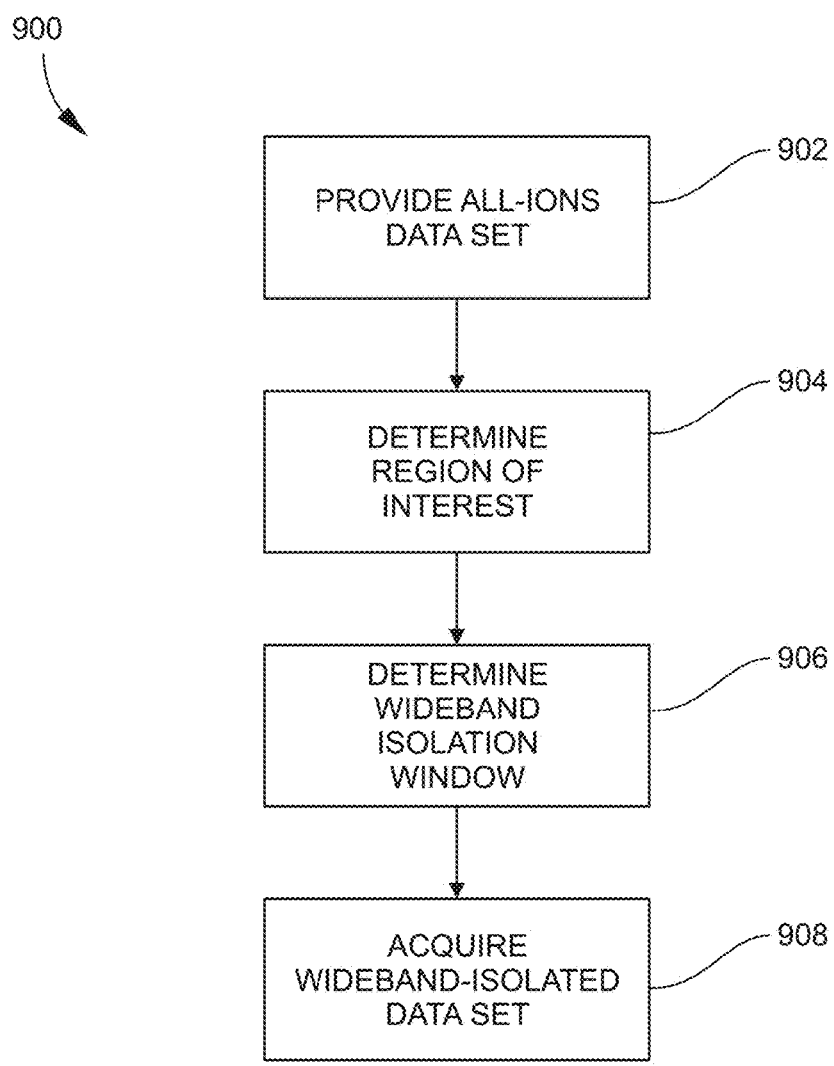
FIG. 9 is a flow diagram illustrating an example of a method for analyzing a sample by ion mobility-mass spectrometry (IM-MS) in an IM-MS system, according to an embodiment disclosed herein.

FIG. 9 is a flow diagram 900 illustrating an example of a method for analyzing a sample by ion mobility-mass spectrometry (IM-MS) in an IM-MS system, according to an embodiment disclosed herein. The IM-MS system utilized to implement the method may be a system as described herein. According to the method, an all-ions data set data acquired from an unfiltered m/z range of ions produced from the sample is provided (step 902). The all-ions data set includes a collection of data points spanning an IM drift time spectrum, an m/z spectrum correlated with the IM drift time spectrum, and ion abundance values correlated with the IM drift time spectrum and the m/z spectrum. A region of interest in the all-ions data set is determined for further analysis (step 904). A wideband isolation window, to be applied by the mass filter to the ions produced from the sample, is determined (step 906). The wideband isolation window may be determined by determining a window width of the wideband isolation window, and determining a sequence of window positions at which the wideband isolation window is to be applied. The window width is an m/z sub-range of the unfiltered m/z range of ions, as described elsewhere herein. In the sequence of window positions, each window position is defined by a drift time value along the IM drift time spectrum and an m/z value along the m/z spectrum, as described elsewhere herein. The window width and the sequence of window positions are determined such that the wideband isolation window, when moved through the sequence of window positions, transmits ions (i.e., covers or captures the IM-MS data corresponding to ions) in the determined region of interest.

A wideband-isolated data set is then acquired (step 908). The wideband-isolated data set may be acquired by transmitting ions produced from the sample through the IM-MS system while operating the mass filter to apply the wideband isolation window. Specifically, ions produced from the sample are transmitted through the IM analyzer. Before or after transmitting the ions through the IM analyzer (depending on whether the IM analyzer is positioned upstream of or downstream from the mass filter), the ions are transmitted into the mass filter. While the ions are transmitted into the mass filter, the mass filter is operated to apply the wideband isolation window having the determined window width, and to move the wideband isolation window through the determined sequence of window positions. In this way, the mass filter outputs mass-filtered ions. The mass-filtered ions, or fragment ions produced from the mass-filtered ions (depending on whether an ion fragmentation device is operated to fragment the mass-filtered ions), are transmitted to the mass analyzer whereby the ions are separated according to m/z ratio. The mass-analyzed ions are then transmitted to the ion detector, which outputs ion measurement signals in response, as appreciated by persons skilled in the art. The wideband-isolated data set, which includes a collection of data points in the determined region of interest, is then produced from the ion measurement signals.

It will be understood that the flow diagram 900 of FIG. 9 may also be representative of an IM-MS system that is configured for carrying out the steps (902-908) described above.

Figure 10:
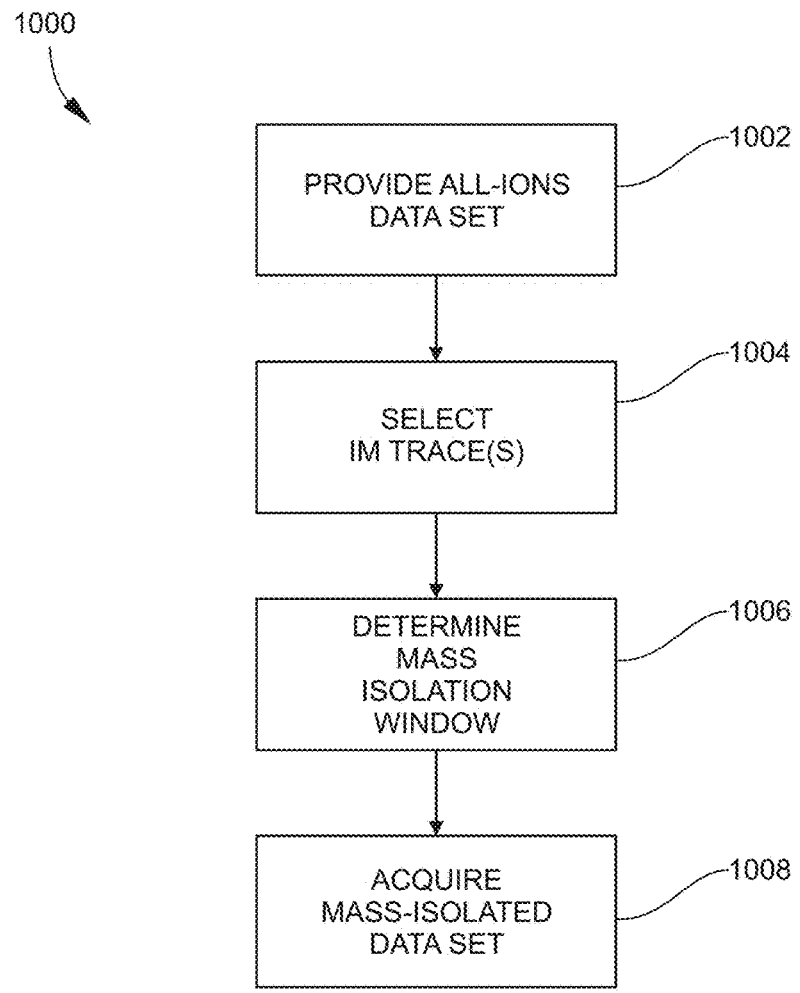
FIG. 10 is a flow diagram 1000 illustrating another example of a method for analyzing a sample by ion mobility-mass spectrometry (IM-MS) in an IM-MS system, according to another embodiment disclosed herein.

FIG. 10 is a flow diagram 1000 illustrating another example of a method for analyzing a sample by ion mobility-mass spectrometry (IM-MS) in an IM-MS system (such as described herein), according to another embodiment disclosed herein. According to the method, an all-ions data set data acquired from an unfiltered m/z range of ions produced from the sample is provided (step 1002). The all-ions data set includes a collection of data points spanning an IM drift time spectrum, an m/z spectrum correlated with the IM drift time spectrum, and ion abundance values correlated with the IM drift time spectrum and the m/z spectrum. Further, the all-ions data set comprises two or more discernable IM traces. As described elsewhere herein, the IM traces may comprise respective sub-collections of data points that map onto the all-ions data set such that the IM traces diverge from each other. One or more of the IM traces are selected for further analysis (step 1004). A mass isolation window, to be applied by the mass filter to the ions produced from the sample, is determined (step 1006). The mass isolation window may be determined by determining a window width of the mass isolation window, and determining a sequence of window positions at which the mass isolation window is to be applied. The window width is an m/z sub-range of the unfiltered m/z range of ions, as described elsewhere herein. In some embodiments the window width may be a wideband window width, as described elsewhere herein. In the sequence of window positions, each window position is defined by a drift time value along the IM drift time spectrum and an m/z value along the m/z spectrum, as described elsewhere herein. The window width and the sequence of window positions are determined such that the mass isolation window, when moved through the sequence of window positions, transmits ions (i.e., covers or captures the IM-MS data corresponding to ions) in the selected IM trace(s).

A mass-isolated data set is then acquired (step 1008), which may be a wideband-isolated data set as described herein. The mass-isolated data set may be acquired by transmitting ions produced from the sample through the IM-MS system while operating the mass filter to apply the mass isolation window. Specifically, ions produced from the sample are transmitted through the IM analyzer. Before or after transmitting the ions through the IM analyzer (depending on whether the IM analyzer is positioned upstream of or downstream from the mass filter), the ions are transmitted into the mass filter. While the ions are transmitted into the mass filter, the mass filter is operated to apply the mass isolation window having the determined window width, and to move the mass isolation window through the determined sequence of window positions. In this way, the mass filter outputs mass-filtered ions. The mass-filtered ions, or fragment ions produced from the mass-filtered ions (depending on whether an ion fragmentation device is operated to fragment the mass-filtered ions), are transmitted to the mass analyzer whereby the ions are separated according to m/z ratio. The mass-analyzed ions are then transmitted to the ion detector, which outputs ion measurement signals in response, as appreciated by persons skilled in the art. The wideband-isolated data set, which includes a collection of data points in the selected IM trace(s), is then produced from the ion measurement signals.

It will be understood that the flow diagram 1000 of FIG. 10 may also be representative of an IM-MS system that is configured for carrying out the steps (1002-1008) described above.

Figure 11:
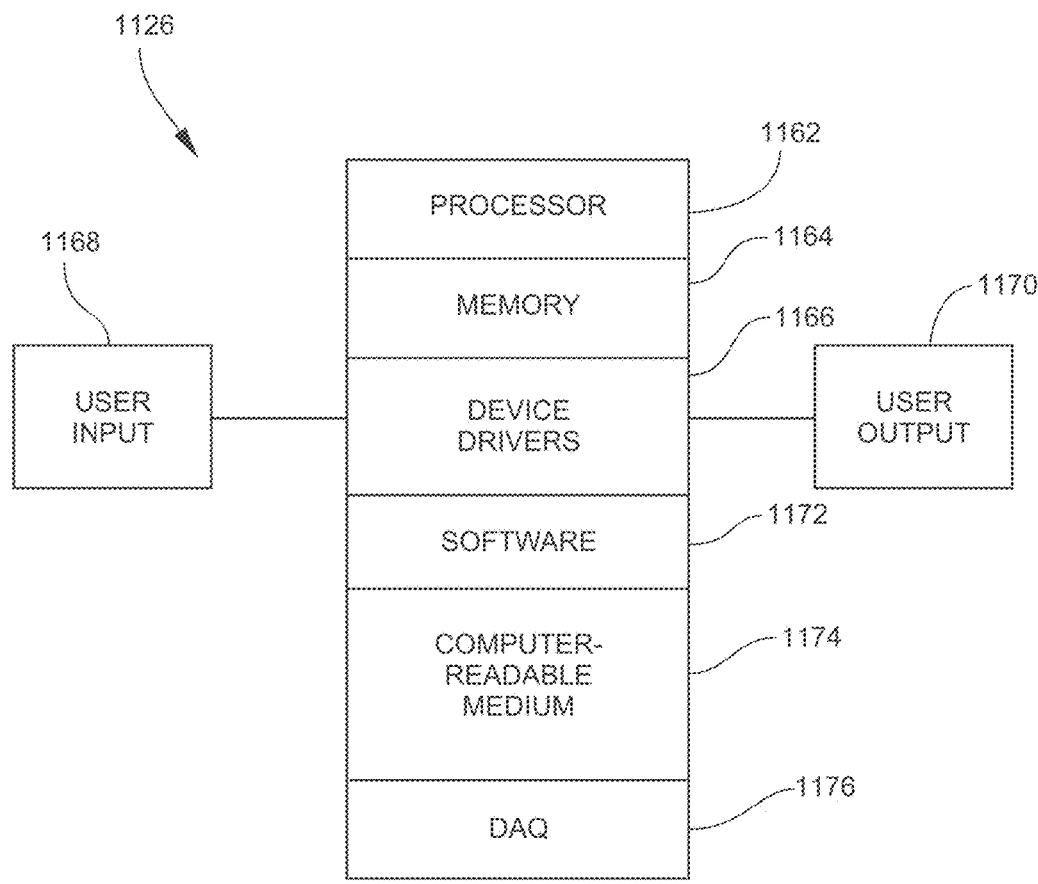
FIG. 11 is a schematic view of an example of a controller or computing device that may be part of or communicate with the IM-MS system illustrated in FIG. 1, according to an embodiment disclosed herein.

FIG. 11 is a schematic view of an example of a controller or computing device 1126 that may be part of or communicate with an IM-MS system according to an embodiment disclosed herein. For example, the controller 1126 may correspond to the controller 126 associated with the IM-MS system 100 illustrated in FIG. 1. In the illustrated embodiment the controller 1126 includes an electronics-based processor 1162, which may be representative of a main electronic processor providing overall control, and one or more electronic processors configured for dedicated control operations or specific signal processing tasks (e.g., a graphics processing unit, or GPU). The controller 1126 also includes one or more memories 1164 (volatile and/or nonvolatile) for storing data and/or software. The controller 1126 may also include one or more device drivers 1166 for controlling one or more types of user interface devices and providing an interface between the user interface devices and components of the controller 1126 communicating with the user interface devices. Such user interface devices may include user input devices 1168 (e.g., keyboard, keypad, touch screen, mouse, joystick, trackball, and the like) and user output devices 1170 (e.g., display screen, printer, visual indicators or alerts, audible indicators or alerts, and the like). The controller 1126 may also include one or more types of computer programs or software 1172 contained in memory 1164 and/or on one or more types of computer-readable media 1174 (e.g., compact disks (CDs), flash drives, etc.). Computer programs or software 1172 may contain instructions (e.g., logic instructions) for performing all or part of any of the methods disclosed herein. Computer programs or software 1172 may include application software and system software. System software may include an operating system (e.g., a Microsoft Windows® operating system) for controlling and managing various functions of the controller 1126, including interaction between hardware and application software. In particular, the operating system may provide a graphical user interface (GUI) as described elsewhere, which is displayable via a user output device 1170 such as a display screen, and with which a user may interact with the use of a user input device 1168 such as a keyboard or a pointing device (e.g., mouse). The controller 1126 may also include one or more data acquisition/signal conditioning components 1176 (as may be embodied in hardware, firmware and/or software) for receiving and processing ion measurement signals outputted by the ion detector 1150, including formatting data for presentation in graphical form by the GUI.

It will be understood that FIGS. 1 and 11 are high-level schematic depictions of an example of an IMS-MS system 100 and associated controller 126 or 1126 consistent with the present disclosure. Other components, such as additional structures, vacuum pumps, gas plumbing, ion optics, ion guides, electronics, and computer-related or electronic processor-related components may be included as needed for practical implementations. It will also be understood that the controller 1126 is schematically represented in FIG. 11 as functional blocks intended to represent structures (e.g., circuitries, mechanisms, hardware, firmware, software, etc.) that may be provided. The various functional blocks and signal links have been arbitrarily located for purposes of illustration only and are not limiting in any manner. Persons skilled in the art will appreciate that, in practice, the functions of the controller 126 or 1126 may be implemented in a variety of ways and not necessarily in the exact manner illustrated in FIGS. 1 and 11 and described herein.

EXEMPLARY EMBODIMENTS

Exemplary embodiments provided in accordance with the presently disclosed subject matter include, but are not limited to, the following:

1. A method for analyzing a sample by ion mobility-mass spectrometry (IM-MS), the method comprising: providing an all-ion data set acquired from an unfiltered m/z range of ions produced from the sample, the all-ions data set comprising a collection of data points spanning an IM drift time spectrum, an m/z spectrum correlated with the IM drift time spectrum, and ion abundance values correlated with the IM drift time spectrum and the m/z spectrum; determining a region of interest in the all-ions data set for further analysis; determining a wideband isolation window to be applied by the mass filter to the ions produced from the sample, by: determining a window width of the wideband isolation window, wherein the window width is an m/z sub-range of the unfiltered m/z range of ions; and determining a sequence of window positions at which the wideband isolation window is to be applied, wherein each window position is defined by a drift time value along the IM drift time spectrum and an m/z value along the m/z spectrum, wherein the window width and the sequence of window positions are determined such that the wideband isolation window when moved through the sequence of window positions transmits ions in the determined region of interest; acquiring a wideband-isolated data set by: transmitting ions produced from the sample through the IM analyzer; before or after transmitting the ions through the IM analyzer, transmitting the ions into the mass filter; while transmitting the ions into the mass filter, operating the mass filter to apply the wideband isolation window having the determined window width, and to move the wideband isolation window through the determined sequence of window positions, wherein the mass filter outputs mass-filtered ions; transmitting the mass-filtered ions, or fragment ions produced from the mass-filtered ions, to the mass analyzer and to the ion detector, wherein the ion detector outputs ion measurement signals; and producing the wideband-isolated data set from the ion measurement signals, wherein the wideband-isolated data set comprises a collection of data points in the determined region of interest.

2. The method of embodiment 1, wherein the window width is selected from the group consisting of: at least 20 m/z; at least 50 m/z; at least 100 m/z; at least 250 m/z; and at least 500 m/z.

3. The method of any of the preceding embodiments, wherein determining the window width comprises determining the window width such that the window width is constant at each window position, or such that the window width at one or more of the window positions is different from the window width at the other window positions.

4. The method of any of the preceding embodiments, wherein the all-ions data set comprises two or more IM traces, and the IM traces comprise respective sub-collections of data points that map onto the all-ions data set such that the IM traces diverge from each other.

5. The method of embodiment 4, wherein determining the region of interest comprises selecting one of the IM traces, and determining the wideband isolation window comprises determining the window width and the sequence of window positions such that the wideband isolation window when moved through the sequence of window positions transmits ions in the selected 1M trace.

6. The method of embodiment 4, wherein determining the region of interest comprises selecting two or more of the IM traces, and determining the wideband isolation window comprises determining the window width and the sequence of window positions such that the wideband isolation window when moved through the sequence of window positions transmits ions in the selected 1M traces.

7. The method of any of the preceding embodiments, wherein determining the sequence of window positions comprises determining a sequence selected from the group consisting of: a sequence in which the window positions are stepped through the region of interest; a sequence in which the window positions are scanned through the region of interest; and a sequence in which the mass sub-ranges of the isolation windows are varied according to a predefined pattern.

8. The method of any of the preceding embodiments, comprising transmitting the mass-filtered ions from the mass filter through an ion fragmentation device to produce fragment ions, wherein the fragment ions are transmitted to the mass analyzer.

9. The method of any of the preceding embodiments, comprising displaying the all-ions data set, wherein determining the region of interest, determining the wideband isolation window, or both determining the region of interest and determining the wideband isolation window, is based at least in part on evaluating the displayed all-ions data set.

10. The method of any of the preceding embodiments, comprising displaying the all-ions data set, wherein determining the region of interest, determining the wideband isolation window, or both determining the region of interest and determining the wideband isolation window, is based at least in part on operating a user-input device to select boundaries of the region of interest.

11. The method of any of the preceding embodiments, wherein determining the region of interest comprises determining a plurality of regions of interest, and wherein the regions of interest are contiguous or non-contiguous with each other.

12. The method of any of the preceding embodiments, wherein providing the all-ions data set comprises acquiring the all-ions data set by: transmitting ions produced from the sample through the IM analyzer; before or after transmitting the ions through the IM analyzer, transmitting the ions through the mass filter without filtering the ions; transmitting the ions, or fragment ions produced from the mass-filtered ions, to the mass analyzer and to the ion detector, wherein the ion detector outputs ion measurement signals; and producing the all-ions data set data set from the ion measurement signals.

13. A method for analyzing a sample by ion mobility-mass spectrometry (IM-MS) in an IM-MS system, wherein the IM-MS system comprises an IM analyzer, a mass filter, a mass analyzer, and an ion detector, the method comprising: providing an all-ions data set acquired from an unfiltered m/z range of ions produced from the sample, the all-ions data set comprising a collection of data points spanning an IM drift time spectrum, an m/z spectrum correlated with the IM drift time spectrum, and ion abundance values correlated with the IM drift time spectrum and the m/z spectrum, wherein the all-ions data set comprises two or more IM traces, and the IM traces comprise respective sub-collections of data points that map onto the all-ions data set such that the IM traces diverge from each other; selecting one or more of the IM traces for further analysis; determining a mass isolation window to be applied by the mass filter to the ions produced from the sample, by: determining a window width of the mass isolation window, wherein the window width is an m/z sub-range of the unfiltered m/z range of ions; and determining a sequence of window positions at which the mass isolation window is to be applied, wherein each window position is defined by a drift time value along the IM drift time spectrum and an m/z value along the m/z spectrum, wherein the window width and the sequence of window positions are determined such that the mass isolation window when moved through the sequence of window positions transmits ions in the one or more selected the IM traces; acquiring a mass-isolated data set by: transmitting ions produced from the sample through the IM analyzer; before or after transmitting the ions through the IM analyzer, transmitting the ions into the mass filter; while transmitting the ions into the mass filter, operating the mass filter to apply the mass isolation window having the determined window width, and to move the mass isolation window through the determined sequence of window positions, wherein the mass filter outputs mass-filtered ions; transmitting the mass-filtered ions, or fragment ions produced from the mass-filtered ions, to the mass analyzer and to the ion detector, wherein the ion detector outputs ion measurement signals; and producing the mass-isolated data set from the ion measurement signals, wherein the mass-isolated data set comprises a collection of data points in the one or more selected the IM traces.

14. The method of embodiment 13, wherein the window width is selected from the group consisting of: at least 5 m/z; at least 20 m/z; at least 50 m/z; at least 100 m/z; at least 250 m/z; and at least 500 m/z.

15. The method of embodiment 13 or 14, wherein determining the window width comprises determining the window width such that the window width is constant at each window position, or such that the window width at one or more of the window positions is different from the window width at the other window positions.

16. The method of any of embodiments 13-15, wherein determining the sequence of window positions comprises determining a sequence selected from the group consisting of: a sequence in which the window positions are stepped through the one or more selected IM traces; a sequence in which the window positions are scanned through the one or more selected IM traces; and a sequence in which the mass sub-ranges of the isolation windows are varied according to a predefined pattern.

17. The method of any of embodiments 13-16, comprising transmitting the mass-filtered ions from the mass filter through an ion fragmentation device to produce fragment ions, wherein the fragment ions are transmitted to the mass analyzer.

18. The method of any of embodiments 13-17, comprising displaying the all-ions data set, wherein selecting the one or more IM traces, determining the mass isolation window, or both selecting the one or more IM traces and determining the mass isolation window, is based at least in part on evaluating the displayed all-ions data set.

19. The method of any of embodiments 13-18, comprising displaying the all-ions data set, wherein selecting the one or more IM traces, determining the wideband isolation window, or both selecting the one or more IM traces and determining the wideband isolation window, is based at least in part on operating a user-input device to select boundaries of the one or more selected IM traces.

20. The method of any of embodiments 13-19, wherein providing the all-ions data set comprises acquiring the all-ions data set by: transmitting ions produced from the sample through the IM analyzer; before or after transmitting the ions through the IM analyzer, transmitting the ions through the mass filter without filtering the ions; transmitting the ions, or fragment ions produced from the mass-filtered ions, to the mass analyzer and to the ion detector, wherein the ion detector outputs ion measurement signals; and producing the all-ions data set data set from the ion measurement signals.

21. An ion mobility-mass spectrometry (IM-MS) system, comprising: an IM analyzer; a mass filter, disposed either upstream of or downstream from the IM analyzer; a mass analyzer disposed downstream from the IM analyzer and the mass filter; an ion detector configured to receive ions from the mass analyzer; and a controller configured to control acquisition of a wideband-isolated data set from a sample, by controlling the mass filter to apply a wideband isolation window to ions produced from the sample such that the wideband isolation window moves through a sequence of window positions effective to capture IM-MS data limited to a region of interest in an all-ions data set, wherein: the all-ions data set comprises a collection of data points previously acquired from an unfiltered m/z range of ions produced from the sample, the collection of data points spanning an IM drift time spectrum, an m/z spectrum correlated with the IM drift time spectrum, and ion abundance values correlated with the IM drift time spectrum and the m/z spectrum; the wideband isolation window has a window width corresponding to an m/z sub-range of the unfiltered m/z range of ions; and each window position is defined by a drift time value along the IM drift time spectrum and an m/z value along the m/z spectrum.

22. The IM-MS system of embodiment 21, wherein the controller is configured for determining, or assisting in determining, a parameter selected from the group consisting of: the region of interest; the window width; the sequence of window positions; a combination of two or more of the foregoing.

23. The IM-MS system of embodiment 21 or 22, wherein the controller is configured for controlling the mass filter to apply the wideband isolation window such that the window width is constant at each window position, or such that the window width at one or more of the window positions is different from the window width at the other window positions.

24. The IM-MS system of any of embodiments 21-23, wherein the controller is configured for controlling the mass filter to apply the wideband isolation window such that the moves through one or more selected IM traces of the all-ions data set.

25. The IM-MS system of any of embodiments 21-24, wherein the sequence of window positions is selected from the group consisting of: a sequence in which the window positions are stepped through the region of interest; a sequence in which the window positions are scanned through the region of interest; and a sequence in which the mass sub-ranges of the isolation windows are varied according to a predefined pattern.

26. The IM-MS system of any of embodiments 21-25, comprising an ion fragmentation device downstream from the mass filter and upstream of the mass analyzer.

27. The IM-MS system of any of embodiments 21-26, wherein the controller is configured for displaying the all-ions data set.

28. The IM-MS system of any of embodiments 21-27, wherein the controller is configured for controlling a graphical user interface that displays the all-ions data set and receives user input defining boundaries of the region of interest.

29. An ion mobility-mass spectrometry (IM-MS) system, comprising: an IM analyzer; a mass filter, disposed either upstream of or downstream from the IM analyzer; a mass analyzer disposed downstream from the IM analyzer and the mass filter; an ion detector configured to receive ions from the mass analyzer; and a controller configured to control acquisition of a mass-isolated data set from a sample, by controlling the mass filter to apply a mass isolation window to ions produced from the sample such that the mass isolation window moves through a sequence of window positions effective to capture IM-MS data limited to one or more selected IM traces of an all-ions data set, wherein: the all-ions data set comprises a collection of data points previously acquired from an unfiltered m/z range of ions produced from the sample, the collection of data points spanning an IM drift time spectrum, an m/z spectrum correlated with the IM drift time spectrum, and ion abundance values correlated with the IM drift time spectrum and the m/z spectrum, wherein the all-ions data set further comprises two or more IM traces, the IM traces comprising respective sub-collections of data points that map onto the all-ions data set such that the IM traces diverge from each other; the mass isolation window has a window width corresponding to an m/z sub-range of the unfiltered m/z range of ions; and each window position is defined by a drift time value along the IM drift time spectrum and an m/z value along the m/z spectrum.

30. The IM-MS system of embodiment 29, wherein the controller is configured for determining, or assisting in determining, a parameter selected from the group consisting of: the one or more IM traces to be captured; the window width; the sequence of window positions; a combination of two or more of the foregoing.

31. The IM-MS system of embodiment 29 or 30, wherein the controller is configured for controlling the mass filter to apply the mass isolation window such that the window width is constant at each window position, or such that the window width at one or more of the window positions is different from the window width at the other window positions.

32. The IM-MS system of any of embodiments 29-31, wherein the sequence of window positions is selected from the group consisting of: a sequence in which the window positions are stepped through the one or more selected IM traces; a sequence in which the window positions are scanned through the one or more selected IM traces; and a sequence in which the mass sub-ranges of the isolation windows are varied according to a predefined pattern.

33. The IM-MS system of any of embodiments 29-32, comprising an ion fragmentation device downstream from the mass filter and upstream of the mass analyzer.

34. The IM-MS system of any of embodiments 29-33, wherein the controller is configured for displaying the all-ions data set.

35. The IM-MS system of any of embodiments 29-34, wherein the controller is configured for controlling a graphical user interface that displays the all-ions data set and receives user input defining boundaries of the one or more selected IM traces.

36. An IM-MS system comprising at least a processor and a memory configured for performing or controlling all or part of the method of any of the preceding embodiments.

37. An IM-MS system comprising: an ion detector; and a controller configured for receiving ion measurement signals from the ion detector, and for performing or controlling all or part of the method of any of the preceding embodiments.

38. A non-transitory computer-readable storage medium, comprising instructions for performing or controlling all or part of the method of any of the preceding embodiments.

39. A system comprising the non-transitory computer-readable storage medium of embodiment 38.

As used herein, an "interface" or "user interface" is generally a system by which users interact with a controller (e.g., a computing device). An interface may include an input (e.g., a user input device) for allowing users to manipulate a controller, and may include an output (e.g., a user output device) for allowing the system to present information and/or data, indicate the effects of the user's manipulation, etc. One example of an interface is a graphical user interface (GUI) that allows users to interact with programs in more ways than typing. A GUI typically may offer display objects, and visual indicators, as opposed to (or in addition to) text-based interfaces, typed command labels or text navigation to represent information and actions available to a user. For example, an interface may be a display window or display object, which is selectable by a user of a controller for interaction. The display object may be displayed on a display screen of a controller and may be selected by and interacted with by a user using the interface. In one non-limiting example, the display of the controller may be a touch screen, which may display a display icon. The user may depress the area of the touch screen at which the display icon is displayed for selecting the display icon. In another example, the user may use any other suitable interface of a controller, such as a keypad, to select the display icon or display object. For example, the user may use a track ball or arrow keys for moving a cursor to highlight and select the display object.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the controller 126 or 1126 schematically depicted in FIG. 1 or 11. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), application specific integrated circuits (ASICs), or field-programmable gate arrays (FPGAs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the controller 126 or 1126 shown in FIG. 1 or 11), direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program may be electronically captured via, for instance, optical scanning of the paper or other medium, then compiled, interpreted, or otherwise processed in a suitable manner if necessary, and then stored in a computer memory or machine memory.

It will also be understood that the term "in signal communication" or "in electrical communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for analyzing a sample by ion mobility-mass spectrometry (IM-MS) in an IM-MS system; wherein the IM-MS system comprises an IM analyzer, a mass filter, a mass analyzer, and an ion detector, the method comprising:
   providing an all-ions data set acquired from an unfiltered m/z range of ions produced from the sample, the all-ions data set comprising a collection of data points spanning an IM drift time spectrum, in m/z spectrum correlated with the IM drift time spectrum, and ion abundance values correlated with the IM drift time spectrum and the m/z spectrum;
   determining a region of interest in the all-ions data set for further analysis;
   determining a wideband isolation window to be applied by the mass filter to the ions produced from the sample, by:
      determining a window width of the wideband isolation window, wherein the window width is an m/z sub-range of the unfiltered m/z range of ions and is at least 20 m/z; and
      determining a sequence of window positions at which the wideband isolation window is to be applied, wherein each window position is defined by a time value along the IM drift time spectrum and an m/z value along the m/z spectrum, wherein the window width and the sequence of window positions are determined such that the wideband isolation window when moved through the sequence of window positions transmits ions in the determined region of interest;

acquiring a wideband-isolated data set by:

transmitting ions produced from the sample through the IM analyzer;

before or after transmitting the ions through the IM analyzer, transmitting the ions into the mass filter;

while transmitting the ions into the mass filter, operating the mass filter to apply the wideband isolation window having the determined window width, and to move the wideband isolation window through the determined sequence of window positions, wherein the mass filter outputs mass-filtered ions;

transmitting the mass-filtered ions, or fragment ions produced from the mass-filtered ions, to the mass analyzer and to the ion detector, wherein the ion detector outputs ion measurement signals; and producing the wideband-isolated data set from the ion measurement signals, wherein the wideband-isolated data set comprises a collection of data points in the determined region of interest.

2. The method of claim 1, wherein the window width is selected from the group consisting of: at least 50 m/z; at least 100 m/z; at least 250 m/z; and at least 500 m/z.

3. The method of claim 1, wherein determining the window width comprises determining the window width such that the window width is constant at each window position, or such that the window width at one or more of the window positions is different from the window width at the other window positions.

4. The method of claim 1, wherein the all-ions data set comprises two or more IM traces, and the IM traces comprise respective sub-collections of data points that map onto the all-ions data set such that the IM traces diverge from each other.

5. The method of claim 4, wherein determining the region of interest comprises selecting one of the IM traces, and determining the wideband isolation window comprises determining the window width and the sequence of window positions such that the wideband isolation window when moved through the sequence of window positions transmits ions in the selected IM trace.

6. The method of claim 4, wherein determining the regions of interest comprises selecting two or entire of the IM traces, and determining the wideband comprises determining the window width and the sequence of window positions such that the wideband isolation window when moved through the sequence of window positions transmits ions in the selected IM traces.

7. The method of claim 1, wherein determining the sequence of window positions comprises determining a sequence selected from the group consisting of:

a sequence in which the window positions are stepped through the region of interest;

a sequence in which the window positions are scanned through the region of interest; and a sequence in which the mass sub-ranges of the isolation windows are varied according to a predefined pattern.

8. The method of claim 1, comprising a step selected from the group consisting of:

displaying the all-ions data set, wherein determining the region of interest, determining the wideband isolation window, or both determining the region of interest and determining the wideband isolation window, is based at least in part on evaluating the displayed all-ions data set;

displaying the all-ions data set, wherein determining the region of interest, determining the wideband isolation window, or both determining the region of interest and determining the wideband isolation window, is based at least in part on operating a user-input device to select boundaries of the region of interest; and both of the foregoing.

9. The method of claim 1, wherein determining the region of interest comprises determining a plurality of regions of interest, and wherein the regions of interest are contiguous or non-contiguous with each other.

10. The method of claim 1, wherein providing the all-ions data set comprises acquiring the all-ions data set by:

transmitting ions produced from the sample through the IM analyzer;

before or after transmitting the ions through the IM analyzer, transmitting the ions through the mass filter without filtering the ions;

transmitting the ions, or fragment ions produced from the mass filtered ions, to the mass analyzer and to the ion detector, wherein the ion detector ion measurement signals; and producing the all-ions data set data set from the ion measurement signals.

11. A method for analyzing sample by ion mobility-mass spectrometry (IM-MS) in an IM-MS system, wherein the IM-MS system comprises IM analyzer, a mass filter, a mass analyzer, and an ion detector, the method comprising:

providing an all-ions data set acquired from an unfiltered m/z range of ions produced from the sample, the all-ions data set comprising a collection of data points spanning an IM drift time spectrum, an m/z spectrum correlated with the IM drift time spectrum and ion abundance values correlated with the IM drift time spectrum and the m/z spectrum, wherein the all-ions data set comprises two or more IM traces, and the IM traces comprise respective sub-collections of data points that map onto the all-ions data set such that the IM traces diverge from each other;

selecting one or more of the IM traces for further analysis;

determining a mass isolation window to be applied by the mass filter to the ions produced from the sample, by:

determining a window width of the mass isolating window wherein the window width is an m/z sub-range of the unfiltered m/z range of ions; and determining a sequence of window positions at which the mass isolation window is to be applied, wherein each window position is defined by a drift time value along the IM drift time spectrum and an m/z value along the m/z spectrum, wherein the window width and the sequence of window positions are determined such that the mass isolation window when moved through the sequence of window positions transmits ions in the one or more selected the IM traces;

acquiring a mass-isolated data set by:

transmitting ions produced from the sample through the IM analyzer;

before or after transmitting the ions through the IM analyzer, transmitting the ions into the mass filter;

while transmitting the ions into the mass filter, operating the mass filter to apply the mass isolation window having the determined window width, and to move the mass isolation window through the determined sequence of window positions, wherein the mass filter outputs mass-filtered ions;

transmitting the mass-filtered ions, or fragment ions produced from the mass-filtered ions, to the mass analyzer and to the ion detector, wherein the ion detector outputs ion measurement signals; and producing the mass-isolated data set from the ion measurement signals, wherein the mass-isolated data set comprises a collection of data points in the one or more selected the IM traces.

12. The method of claim 11, wherein the window width is selected from the group consisting of: at least 5 m/z; at least 20 m/z; at least 50 m/z; at least 100 m/z; at least 250 m/z; and at least 500 m/z.

13. The method of claim 11, wherein determining the sequence of window positions comprises determining a sequence selected from the group consisting of:
   a sequence in which the window positions are scanned through the one or more selected IM traces;
   a sequence in which the window positions are scanned through the one or more selected IM tikes; and
   a sequence in which the mass sub-ranges of the isolation windows are varied according to a predefined pattern.

14. The method of claim 11, comprising a step selected from the group consisting of:
   displaying the all-ions data set, wherein selecting the one or more IM traces, determining the mass isolation window, or both selecting the one or more IM traces and determining the mass isolation window, is based at least in part on evaluating the displayed all-ions data set;
   displaying the all-ions data set, wherein selecting the one or more IM traces, determining the wideband isolation window, or both selecting the one or more IM traces and determining the wideband isolation window, is based at least in part on operating a user-input device to select boundaries of the one or more selected IM traces;
   both of the foregoing.

15. An ion mobility-mass spectrometry (IM-MS) system, comprising:
   an IM analyzer;
   a mass filter, disposed either upstream of or downstream from the IM analyzer;
   a mass analyzer disposed downstream from the IM analyzer and the mass filter;
   an ion detector configured to receive ions from the mass analyzer; and
   a controller configured to:
   receive an all-ions data set acquired from an unfiltered m/z range of ions produced from the sample, the all-ions data set comprising a collection of data points spanning an IM drift time spectrum, an m/z spectrum correlated with the IM drift time spectrum, and ion abundance values correlated with the IM drift time spectrum and the m/z spectrum; and
   control acquisition of a wideband-isolated data set by:
      controlling transmitting ions produced from the sample through the IM analyzer;
      before or after transmitting the ions through the IM analyzer, controlling transmitting the ions into the mass filter;
      while transmitting the ions into the mass filter, controlling operating the mass filter to apply a wideband isolation window having a window width, and to move the wideband isolation window through a sequence of window positions, wherein the mass filter outputs mass-filtered ions;
      controlling transmitting the mass-filtered ions, or fragment ions produced from the mass-filtered ions, to the mass analyzer and to the ion detector, wherein the ion detector outputs ion measurement signals; and
      controlling producing the wideband-isolated data set from the ion measurement signals, wherein the wideband-isolated data set comprises a collection of data points in a region in the all-ions data set determined to be a region of interest for further analysis,
      wherein the wideband isolation window is determined by:
         determining the window width, wherein the window width is an m/z sub-range of the unfiltered m/z range of ions; and
         determining the sequence of window positions, wherein each window position is defined by a drift time value along the IM drift time spectrum and an m/z value along the m/z spectrum,
      wherein the window width and the sequence of window positions are determined such that the wideband isolation window when moved through the sequence of window positions transmits ions in the region of interest.

16. The IM-MS system of claim 15, wherein the controller is configured for determining, or assisting in determining, a parameter selected from the group consisting of: the region of interest; the window width, the sequence of window positions; as combination of two or more of the foregoing.

17. The IM-MS system of claim 15, wherein the controller is configured for controlling the mass filter to apply the wideband isolation window such that the wideband isolation window moves through one or more selected IM traces of the all-ions data set.

18. The IM-MS system of claim 15, wherein the sequence of window positions is selected from the group consisting of:
   a sequence in which the window positions are stepped through the region of interest;
   a sequence in which the window positions are scanned through the region of interest; and
   a sequence in which the mass sub-ranges of the isolation windows are varied to a predefined pattern.

19. The IM-MS system of claim 15, comprising an ion fragmentation device downstream from the mass filter and upstream of the mass analyzer.

20. The IM-MS system of claim 15, wherein the controller is configured for performing a step selected from the group consisting of:
   displaying the all-ions data set;
   controlling a graphical user interface that displays the data set and receives user input defining boundaries of the region of interest;
   both of the foregoing.

* * * * *